(12) United States Patent
Abel et al.

(10) Patent No.: US 11,562,808 B2
(45) Date of Patent: Jan. 24, 2023

(54) RATIONAL DRUG DESIGN WITH COMPUTATIONAL FREE ENERGY DIFFERENCE CALCULATION USING A MODIFIED BOND STRETCH POTENTIAL

(71) Applicant: Schrödinger, LLC, New York, NY (US)

(72) Inventors: Robert Abel, Brooklyn, NY (US); Lingle Wang, New York, NY (US)

(73) Assignee: Schrödinger, Inc., New York, NY (US)

( * ) Notice: Subject to any disclaimer, the term of this patent is extended or adjusted under 35 U.S.C. 154(b) by 450 days.

(21) Appl. No.: 16/595,758

(22) Filed: Oct. 8, 2019

(65) Prior Publication Data

US 2020/0286594 A1  Sep. 10, 2020

Related U.S. Application Data

(63) Continuation of application No. 14/138,186, filed on Dec. 23, 2013, now abandoned.

(51) Int. Cl.
| | | |
|---|---|---|
| *G01N 33/48* | (2006.01) | |
| *G01N 33/50* | (2006.01) | |
| *G16C 20/30* | (2019.01) | |
| *G16B 15/00* | (2019.01) | |
| *G16B 15/30* | (2019.01) | |
| *G16C 20/10* | (2019.01) | |

(52) U.S. Cl.
CPC ............. *G16C 20/30* (2019.02); *G16B 15/00* (2019.02); *G16B 15/30* (2019.02); *G16C 20/10* (2019.02)

(58) Field of Classification Search
CPC ........ G16C 20/30; G16C 20/10; G16B 15/00; G16B 15/30
See application file for complete search history.

(56) References Cited

U.S. PATENT DOCUMENTS

| | | |
|---|---|---|
| 2003/0055574 A1 | 3/2003 | Still et al. |
| 2007/0118296 A1 | 5/2007 | Santalucia |
| 2015/0178442 A1 | 6/2015 | Abel |
| 2015/0317459 A1 | 11/2015 | Farhi et al. |
| 2017/0220717 A1 | 8/2017 | Matubayasi et al. |
| 2019/0065697 A1 | 2/2019 | Wang |

FOREIGN PATENT DOCUMENTS

| | | |
|---|---|---|
| EP | 2509015 | 10/2012 |
| JP | 2012190423 | 10/2012 |

OTHER PUBLICATIONS

Brooks et al. CHARMM: A program for macromolecular energy, minimization, and dynamics calculations. Journal of Computational Chemistry, vol. 4, pp. 187-217. (Year: 1983).*

Beutler et al., "Avoiding singularities and numerical instabilities in free energy calculations based on molecular simulations," Chem. Phys. Lett., 1994, 222:529-539.
Knight et al., "λ-dynamics free energy simulation methods", J. Comput. Chem., Aug. 2009, 30(11):1-16.
International Preliminary Report on Patentability in International Application No. PCT/US2018/047238, dated Feb. 25, 2020, 7 pages.
"Drug Design"; https://en.wikipedia.org/wiki/Drug_design; retrieved on Jul. 17, 2016; 9 pp.
Golebiowski et al.; "Synthesis of Quaternary a-Amino Acid-based Arginase Inhibitors via the Ugi Reaction"; Bioorganic & Medicinal Chemistiy Letters 23 (2013) 4837-4841.
Wang et al., "Accurate and Reliable Prediction of Relative Ligand Binding Potency in Prospective Drug Discovery by Way of a Modem Free-Energy Calculation Protocol and Force Field", J. Am. Chem. Soc. 2015, 137, 2695-2703 at 2695-6.
Moroney; Drug Action; http://www.merckmanuals.com/home/drugs/drug-dynamics/drug-action; Merck Manual; retrieved on Jul. 14, 2016.
Richardson et al., "Benzopyrans as selective estrogen receptor β agonists (SERBAs). Part 3; Synthesis of cyclopentanone and cyclohexanone intermediates for C-ring modification", Bioorganic & Medicinal Chemistiy Letters 17 (2007) 4824-4828.
Boresh et al., 1998, "The Role of Bonded Terms in Free Energy Simulations: 1. Theoretical Analysis", The Journal of Physical Chemistiy, 103(1):103-118.
Kollman, 1993, "Free Energy Calculations: Applications to Chemical and Biochemical Phenomena", Chemical Reviews, American Chemical Society, 93(7):2395-2417.
Smith, 1997, "A Conformational Study of 2-0xanol: Insight into the Role of Ring Distortion on Enzyme-Catalyzed Glycosidic Bond Cleavage", Journal of the American Chemical Society. 119(11):2699-2706.
PCT International Search Report and Written Opinion from PCT/US2013/077372 dated Jul. 7, 2014, 11 pages.
Liu et al., 1996, "Estimating the Relative Free Energy of Different Molecular States with Respect to a Single Reference State", The Journal of Physical Chemistry, 100(22):9485-9494.
Beroza et al. Protonation of +A11:A21 interacting residues in a protein by a Monte Carlo method: Application to lysozyme and the photosynthetic reaction center of Rhodobacter sphaeroides. PNAS, 1991, vol. 88, pp. 5804-5808.

(Continued)

*Primary Examiner* — Russell S Negin
(74) *Attorney, Agent, or Firm* — Fish & Richardson P.C.

(57) ABSTRACT

A method and system for calculating the free energy difference between a target state and a reference state. The method includes determining one or more intermediate states using a coupling parameter, performing molecular simulations to obtain ensembles of micro-states for each of the system states, and calculating the free energy difference by an analysis of the ensembles of micro-states of the system states. The method can be particularly suited for calculating physical or non-physical transformation of molecular systems such as ring-opening, ring-closing, and other transformations involving bond breaking and/or formation. A soft bond potential dependent on a bond stretching component of the coupling parameter and different from the conventional harmonic potential is used in the molecular simulations of the system states for the bond being broken or formed during the transformation.

21 Claims, 8 Drawing Sheets

(56) References Cited

OTHER PUBLICATIONS

Tester et al. Thermodynamics and Its Applications, 3rd edition. Upper Saddle River, New Jersey: Prentice Hall PTR, 1997, pp. 441-447.
Brooks et al. CHARMM: A program for macromolecular energy, minimization, and dynamics calculation. Journal of Computational Chemistry, 1983, vol. 4, pp. 187-217.
Quinone, 2005, 2 pages. The crystal reference encyclopedia. Obtained online on Jun. 30, 2014 from <<http://www.credoreference.com>>.
Li et al. Forging the missing link in free energy estimations—lambda-WHAM in thermodynamic integration, overlap histogramming, and free energy perturbation. Chemical Physics Letters, vol. 440, 2007, pp. 155-159.
Garate et al., "Free-Energy Differences between States with Different Conformational Ensembles," Journal of Computational Chemistry, vol. 34, dated Jun. 5, 2013, 11 pages.
Riniker et al., "Calculation of Relative Free Energies for Ligand-Protein Binding, Solvation, and Conformational Transitions Using the GROMOS Software," Journal of Physical Chemistry B, vol. 115 No. 46, dated Nov. 24, 2011, 8 pages.
Wikipedia.org [online]. "Statistical ensemble," Nov. 16, 2017, [retrieved on Feb. 19, 2017], Retrieved from the Internet: URL<https://en.wikipedia.org/wiki/Statistical_ensemble_(mathematical_physics)> 9 pages.
Wikipedia.org [online]. "Canonical ensemble," Jan. 11, 2018, [retrieved on Feb. 19, 2017], Retrieved from the Internet: URL<https://en.wikipedia.org/wiki/Canonical_ensemble> 8 pages.
Wikipedia.org [online]. "Isothermal-isobaric ensemble," Sep. 18, 2014, [retrieved on Feb. 19, 2017], Retrieved from the Internet: URL<https://en.wikipedia.org/wiki/Isothermal%E2%80%93isobaric_ensemble> 1 page.
Wikipedia.org [online]. "Grand canonical ensemble," Dec. 24, 2017, [retrieved on Feb. 19, 2017]. Retrieved from the Internet: URL<https://en.wikipedia.org/wiki/Grand_canonical_ensemble> 11 pages.
Wikipedia.org [online]. "Microcanonical ensemble," Sep. 13, 2017, [retrieved on Feb. 19, 2017]. Retrieved from the Internet: URL< https://en.wikipedia.org/wiki/Microcanonical_ensemble> 7 pages.
Wikipedia.org [online]. "Bennett acceptance ratio," Aug. 17, 2017, [retrieved on Feb. 19, 2017], Retrieved from the Internet: URL<https://en.wikipedia.org/wiki/Bennett_acceptance_ratio> 5 pages.
Wikipedia.org [online]. "Thermodynamic integration," Sep. 18, 2017, [retrieved on Feb. 19, 2017]. Retrieved from the Internet: URL<https://en.wikipedia.org/wiki/Thermodynamic_integration> 1 page.
Wikipedia.org [online]. "Interval (mathematics)," Dec. 19, 2017, [retrieved on Feb. 19, 2017], Retrieved from the Internet: URL<https://en.wikipedia.org/wiki/Interval_(mathematics)> 7 pages.
Wang et al., "Absolute Binding Free Energy Calculations Using Molecular Dynamics Simulations with Restraining Potentials," Biophysical Journal, dated Oct. 2006, 17 pages.
Mobley et al., "Perspective-Alchemical free energy calculations for drug discovery", J. 1-22 Chem. Phys., dated Dec. 21, 2012, 12 pages.
AlchemistryWiki [online]. "Weighted histogram analysis method," Jul. 17, 2013, [retrieved on Feb. 19, 2017], Retrieved from the Internet: URL<http://www.alchemistry.org/wiki/Weighted_Histogram_Analysis_Method> 3 pages.
Response to Rule 161(1) and 162 EPC Communication dated Aug. 31, 2016 in European Application No. 13829025.9, dated Mar. 8, 2017, 13 pages (with English translation).
International Preliminary Report on Patentablity in International Application No. PCT/US2013/077372, dated Jun. 28, 2016, 9 pages (with English translation).
PCT International Search Report in International Application No. PCT/US 18/47238, dated Nov. 9, 2018, 3 pages.

\* cited by examiner

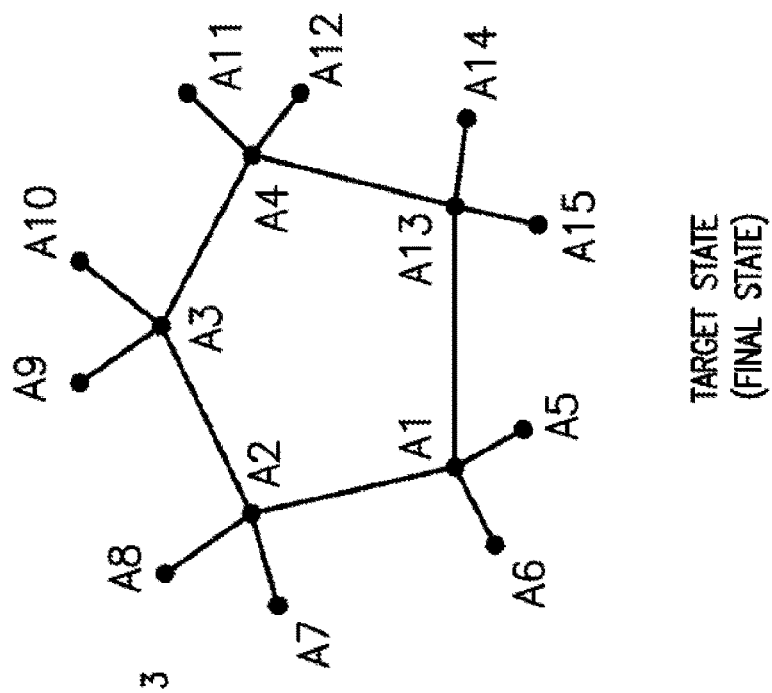
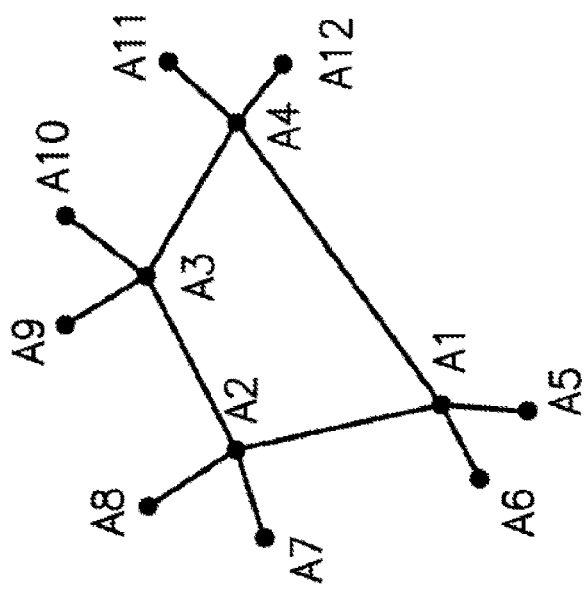
FIG.1c

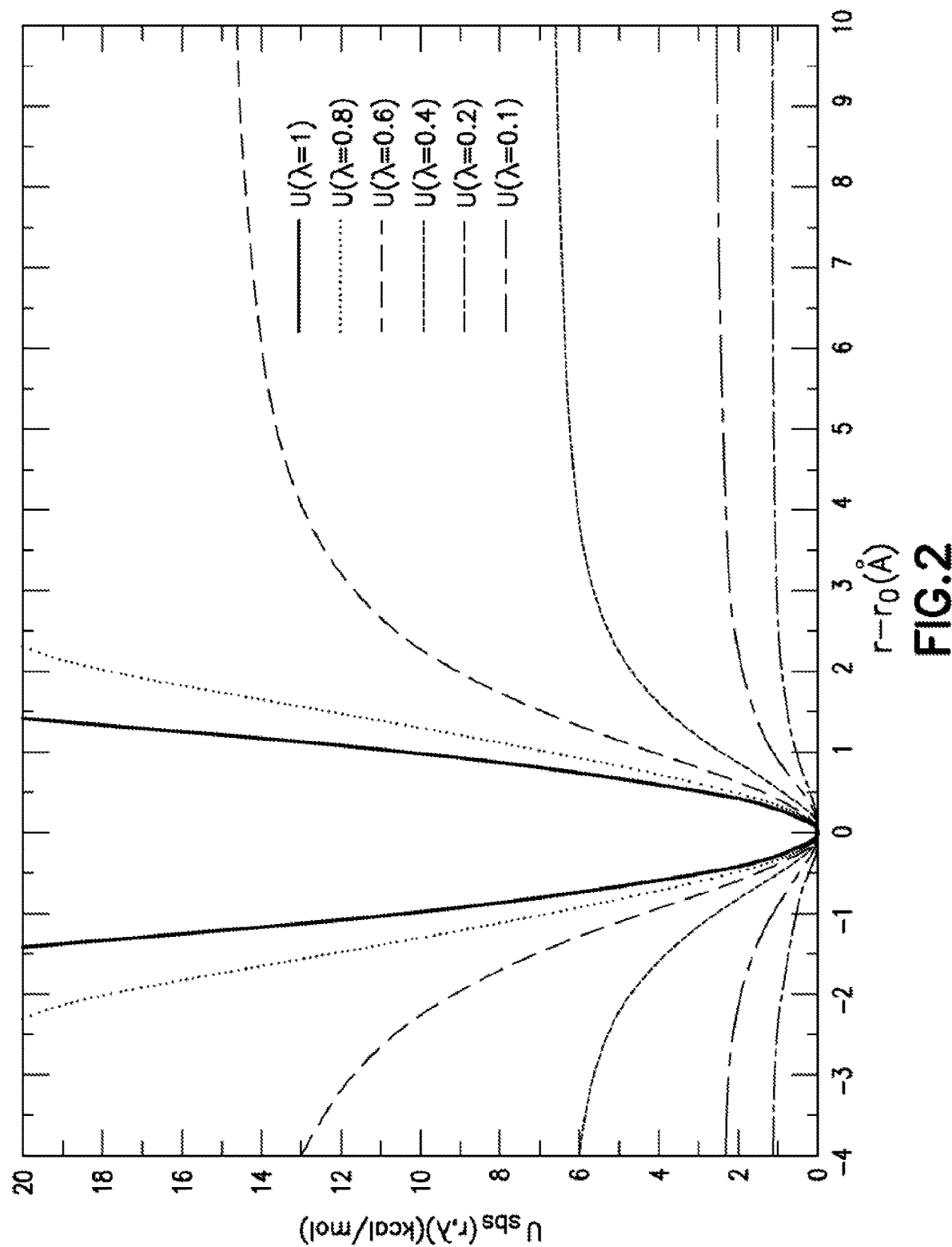

RATIONAL DRUG DESIGN WITH COMPUTATIONAL FREE ENERGY DIFFERENCE CALCULATION USING A MODIFIED BOND STRETCH POTENTIAL

BACKGROUND

Free energy is a fundamental molecular property that plays an essential role in characterizing chemical and biological systems. An understanding of the free energy behavior of many chemical and biochemical processes, such as protein-ligand binding, can be of critical importance in endeavors such as rational drug design (which involves the design of small molecules that bind to a biomolecular target).

Computer modeling and simulations are often used in free energy studies. In most instances, evaluation of accurate absolute free energies from simulations is extremely difficult, if at all possible. Hence, the free energy difference between two well-delineated thermodynamic states, or relative free energy, are often used as a study system to provide insight to particular systems, such as a relative binding affinity of a ligand predicated on the measured affinity of a different but similar ligand (e.g., a congeneric ligand).

In the relative free energy calculations, the two thermodynamic states can be referred to as a reference system state and a target system state, which can represent respectively an initial state of a molecular system, such as a first molecule, and an ending state of the molecule after one or more transformations have taken place (such as a conformational change, topological change, or a replacement of one atom or chemical group with another (i.e., a mutation)). It is noted that such transformations may not always represent realistic physical transformations, but may involve nonphysical or "alchemical" transformations. Different frameworks have been developed for calculating free energy differences, such as free energy perturbations (FEP), thermodynamic integrations (TI), and umbrella sampling.

Within the FEP framework, the free energy difference $\Delta F_{a \to b}$ between the two system states a and b can be expressed by:

$$\Delta F_{a \to b} = -\frac{1}{\beta} \ln \langle \exp\{-\beta[\mathcal{H}_b(x, p_x) - \mathcal{H}_a(x, p_x)]\} \rangle_a \quad (1)$$

where $\beta^{-1} = k_B T$, where is $k_B$ is the Boltzmann constant, T is the temperature. $\mathcal{H}_a(x, p_x)$ and $\mathcal{H}_b(x, p_x)$ are the Hamiltonians characteristic of states a and b respectively. $\langle \ldots \rangle_a$ denotes an ensemble average over configurations representative of the initial, reference state, a.

In practical applications of FEP, the transformation between the two thermodynamic states is usually achieved by a series of transformations between non-physical, intermediate states along a well-delineated pathway that connects a to b. This pathway is often characterized by a general extent parameter, often referred to as a coupling parameter, $\lambda$, which varies from 0 to 1 from the reference state to the target state, and relates the Hamiltonians of the two states by:

$$\mathcal{H}(\lambda) = (1-\lambda)\mathcal{H}_a + \lambda \mathcal{H}_b \quad (2)$$

where $\mathcal{H}(\lambda)$ is the $\lambda$-coupled or hybrid Hamiltonian of the system between the two states (including the two states, when $\lambda$ takes the end values of 0 and 1). Hence, the free energy difference $\Delta F_{a \to b}$ between a and b will be:

$$\Delta F_{a \to b} = -\frac{1}{\beta} \ln \langle \exp\{-\beta[\mathcal{H}(\lambda=1) - \mathcal{H}(\lambda=0)]\} \rangle_{\lambda=0} \quad (3)$$

$$= -\frac{1}{\beta} \sum_{i=0}^{N-1} \ln \langle \exp\{-\beta[\mathcal{H}(x, p_x; \lambda_{i+1}) - \mathcal{H}(x, p_x; \lambda_i)]\} \rangle_i$$

where N stands for the number of "windows" between neighboring states between the reference (initial) state and the target (final) state, and $\lambda_i$ is the values of the coupling parameter in the initial, intermediate, and final state.

The free energy difference between the reference system state a and the target system state b can also be calculated using thermodynamic integration method, where the free energy difference is calculated using the following formula:

$$\Delta F_{a \to b} = \int_{\lambda=0}^{\lambda=1} d\lambda \left\langle \frac{\partial \mathcal{H}(\lambda)}{\partial \lambda} \right\rangle_\lambda \quad (4)$$

where $\lambda$ is the coupling parameter which varies from 0 to 1 from the reference state to the target state, $\mathcal{H}(\lambda)$ is the $\lambda$-coupled or hybrid Hamiltonian of the system between the two states (including the two states, when $\lambda$ takes the end values of 0 and 1), and $$\frac{\partial \mathcal{H}(\lambda)}{\partial \lambda}$$

is the first derivative of the coupled Hamiltonian with respect to the coupling parameter $\lambda$. In practical applications of TI, the transformation between the reference system state and the target system state is achieved by a series transformations along a well-delineated pathway that connects a to b, and the ensemble average of $$\frac{\partial \mathcal{H}(\lambda)}{\partial \lambda}$$

is calculated for all the states sampled, including the reference system state, the intermediate non-physical states, and the target system state. The free energy difference between the reference system state and the target system state is then approximated by numerical integration of the above integral based on the value of the $$\left\langle \frac{\partial \mathcal{H}(\lambda)}{\partial \lambda} \right\rangle_{\lambda_i},$$

where $\lambda_i$ is the values of the coupling parameter in the initial, intermediate, and final states.

Under conventional methods, calculating the free energy to open a ring of a molecule into a linear structure or close a linear structure of a molecule to form a ring can be difficult. In these cases, the reversible work of turning on and off a valence bond connecting two ring atoms needs to be computed. Although one possible approach might be to annihilate a whole ring and grow a corresponding linear structure from scratch, it is computationally very inefficient and sometimes impossible when the ring is very large or the ring is fused with other rings.

SUMMARY OF THE INVENTION

In some embodiments of the invention, a computer-implemented method for computing the free energy difference between a reference state and a target state is provided. The reference state and target state each include a common set of atoms $P_{AB}$. The reference state further includes a set of atoms $P_A$, and the target state further includes a set of atoms $P_B$. The set $P_A$ is present only in the reference state and not in the target state, and the set $P_B$ being present only in the target state and not the reference state. There exist at least two atoms $A_a$ and $A_b$, $A_a$ and $A_b$ are either: (1) not valence-bonded to each other in the reference state and valence-bonded in the target state, or (2) valence-bonded to each other in reference state and not valence-bonded to each other in the target state. The method comprises:

(a) providing a topology, including the bonded connections between the atoms and the relative spatial arrangements of the atoms, for all the atoms in $P_A$, $P_B$, and $P_{AB}$;

(b) determining one or more intermediate system states along a transformation path between the reference state and the target state, the transformation path defined by a coupling parameter $\lambda$ that modulates the energies arising from inter-atom interactions for each system state, the coupling parameter $\lambda$ including a plurality of components each having a value belonging to [0,1] and modulating a different type of interaction energy;

(c) performing, using at least one computer processor, molecular simulations, such as Monte Carlo simulations or molecular dynamics simulations, to obtain ensembles of micro-states for the reference state, the target state, and the intermediate states, wherein performing molecular simulations for each of the system states includes calculating a bonded stretch interaction energy between the atoms $A_a$ and $A_b$, the bonded stretch interaction energy being defined by a soft bond potential; and (d) calculating, using at least one computer processor, the free energy difference between the reference state and the target state, by way of an analysis of the ensembles of micro-states obtained at the target state, the reference state, and the intermediate states.

In some embodiments of the method, the soft bond potential is a function of a bonded stretch component, $\lambda_{sbs}$, of the coupling parameter $\lambda$, and does not include any singular regions for all values of $\lambda_{sbs}$ within [0,1] and for all values of the distance r between $A_a$ and $A_b$. The soft bond potential further satisfy the following conditions: when $\lambda_{sbs}$ is within (0,1), the soft bond potential is flat when the distance between $A_a$ and $A_b$ approaches infinity; when $A_a$ and $A_b$ are not valence bonded in either the reference state or the target state, the soft bond potential is flat and zero for all distances between $A_a$ and $A_b$, and when $A_a$ and $A_b$ are valence bonded in either the target state or the reference state, the soft bond potential reverts to a harmonic potential.

In one embodiment of the method, the first derivative of the soft bond potential with respect to $\lambda_{sbs}$ is continuous and bounded for all values of $\lambda_{sbs}$ between 0 and 1 and for all values of the distance r between $A_a$ and $A_b$. In another embodiment, both the first derivative and the second derivative of the soft bond potential with respect to the distance r between $A_a$ and $A_b$ are continuous and bounded for all values of $\lambda_{sbs}$, and approach zero when r approaches infinity.

In some embodiments of the method, the soft bond potential is a function of $(r-r_0)^2$, where $r_0$ is the equilibrium distance between $A_a$ and $A_b$. In one embodiment, the soft bond potential is expressed by:

$$U_{sbs}(r, \lambda_{sbs}) = \frac{1}{2} kf(\lambda_{sbs})(r-r_0)^2 \frac{1}{1 + g(\lambda_{sbs})\alpha(k, \lambda_{sbs})(r-r_0)^2}$$

where k is a constant, and the functions $f$, $g$ and $\alpha$ are each continuous functions and satisfy the following conditions:

$f(\lambda_{sbs}=0)=0$, $f(\lambda_{sbs}=1)=1$, $g(\lambda_{sbs}=0)=1$, $g(\lambda_{sbs}=1)=0$, $\alpha(k, \lambda_{sbs}<1)>0$.

In particular embodiments, $f(\lambda_{sbs})=\lambda_{sbs}$, $g(\lambda_{sbs})=1-\lambda_{sbs}$, and $\alpha(k, \lambda_{sbs})$ is a nonnegative constant.

In some embodiments, performing molecular simulations for each of the system states comprises: if $A_a$ and $A_b$ are valence-bonded to each other in the reference state and not valence-bonded in the target state, using a schedule of $\lambda_{sbsA}$ and a corresponding soft bond potential for calculating the bonded stretch interaction energy between $A_a$ and $A_b$ for each of the intermediate states, wherein $\lambda_{sbsA}$ is 1 at the reference state, 0 at the target state, and varied from 1 to 0 at each intermediate state along the transformation from the reference state to the target state; and if $A_a$ and $A_b$ are not valence-bonded to each other in the reference state and valence-bonded in the target state, using a schedule of $\lambda_{sbsB}$ and a corresponding soft bond potential for each of the intermediate states and a soft bond potential corresponding to the $\lambda_{sbsB}$ for calculating the bonded stretch interaction between $A_a$ and $A_b$, wherein $\lambda_{sbsB}$ is 0 at the reference state, 1 at the target state, and varied from 0 to 1 at each intermediate state along the transformation from the reference state to the target state.

In some embodiments of the method, performing molecular simulations for each of the system states further comprises:

(a) computing a bonded angle interaction, using applicable parameters for bonded angle interactions of a force field, between (i) a bond formed by $A_a$ and another atom $A_c$, and (ii) the bond between $A_a$ and $A_b$ that is being broken or formed by the transformation from the reference state to the target state;

(b) if $A_a$ and $A_b$ are valence-bonded to each other in the reference state and not valence-bonded to each other in the target state, multiplying the computed bonded angle interaction obtained in (a) by a bonded angle coupling parameter $\lambda_{baA}$, wherein $\lambda_{baA}$ is 1 at the reference state, 0 at the target state, and varied from 1 to 0 at each intermediate state along the transformation from the reference state to the target state; and if $A_a$ and $A_b$ are not valence-bonded to each other in the reference state and valence-bonded to each other in the target state, multiplying the computed bonded angle interaction obtained in (a) by a bonded angle coupling parameter $\lambda_{baB}$, wherein $\lambda_{baB}$ is 0 at the reference state, 1 at the target state, and varied from 0 to 1 at each intermediate state along the transformation from the reference state to the target state; and (c) including the bonded angle interaction obtained in (b) into the total energy of a simulation step of the corresponding system state, In some embodiments of the method, performing molecular simulations for each of the system states further includes:

(a) computing a dihedral angle interaction, using applicable parameters for dihedral interactions of a force field, of a group of four connected atoms $\{A_i, A_j, A_k, A_l\}$, the group including both $A_a$ and $A_b$;

(b) if $A_a$ and $A_b$ are valence-bonded to each other in the reference state and not valence-bonded to each other in the target state, multiplying the computed dihedral interaction obtained in (a) by a dihedral angle coupling parameter $\lambda_{bdA}$, wherein $\lambda_{bdA}$ is 1 at the reference state, 0 at the target state, and varied from 1 to 0 at each intermediate state along the transformation from the reference state to the target state; and if $A_a$ and $A_b$ are not valence-bonded to each other in the reference state and valence-bonded to each other in the target state, multiplying the computed dihedral interaction obtained in (a) by a dihedral angle coupling parameter $\lambda_{bdB}$, wherein $\lambda_{bdB}$ is 0 at the reference state, 1 at the target state, and varied from 0 to 1 at each intermediate state along the transformation from the reference state to the target state; and (c) including the dihedral interaction obtained in (b) into the total energy of the simulation step of the corresponding system state.

In the above embodiments, if $A_a$ and $A_b$ are valence-bonded to each other in the reference state and not valence-bonded to each other in the target state, the bonded angle interaction and the bonded dihedral interaction coupling parameters $\lambda_{baA}$ and $\lambda_{bdA}$, can be each selected to be 0 when $\lambda_{sbsA}$ is smaller than a predefined threshold, and if $A_a$ and $A_b$ are not valence-bonded to each other in the reference state and valence-bonded to each other in the target state, the bonded angle interaction and the bonded dihedral interaction coupling parameters $\lambda_{baB}$ and $\lambda_{bdB}$ can be each selected to be 0 when $\lambda_{sbsB}$ is smaller than a predefined threshold.

In some embodiments of the method, performing molecular simulations for all of the states further includes:

(a) computing nonbonded electrostatic interactions and van der Waals interactions, using applicable parameters for electrostatic interactions and van der Waals interactions of a force field, between two atoms $A_i$ and $A_j$ and the non-bonded exclusion status of the pair $(A_i, A_j)$ is affected by the transformation from the reference state to the target state;

(b) if $A_a$ and $A_b$ are valence-bonded to each other in the reference state and not valence-bonded in the target state, and the nonbonded interactions between $A_i$ and $A_j$ are excluded in the reference state but not excluded in the target state, multiplying the nonbonded electrostatic interactions and van der Waals interactions between $A_i$ and $A_j$ obtained in (a) by coupling parameters $\lambda_{elecAex}$ and $\lambda_{vdwAex}$, respectively, wherein both of $\lambda_{elecAex}$ and $\lambda_{vdwAex}$ are 0 at the reference state, 1 at the target state, and varied from 0 to 1 at each intermediate state along the transformation from the reference state to the target state;

if $A_a$ and $A_b$ are not valence-bonded to each other in the reference state and valence-bonded in the target state, and the nonbonded interactions between $A_i$ and $A_j$ are not excluded in the reference state but excluded in the target state, multiplying the nonbonded electrostatic interactions and van der Waals interactions between $A_i$ and $A_j$ obtained in (a) by coupling parameters $\lambda_{elecBex}$ and $\lambda_{vdwBex}$, respectively, wherein both of $\lambda_{elecBex}$ and $\lambda_{vdwBex}$ are 1 at the reference state, 0 at the target state, and varied from 1 to 0 at each intermediate state along the transformation from the reference state to the target state; and (c) including the calculated nonbonded electrostatic interactions and van der Waals interactions obtained in (b) into the total energy of the simulation step of the corresponding system state.

In some embodiments of the method, wherein performing molecular simulations for all of the states further includes:

if $A_a$ and $A_b$ are valence-bonded to each other in the reference state and not valence-bonded in the target state, and the nonbonded interactions between $A_i$ and $A_j$ are excluded in the reference state but not excluded in the target state, varying each of $\lambda_{elecAex}$ and $\lambda_{vdwAex}$ according to a schedule for each of the intermediate states along the transformation from the reference state to the target state such that when $\lambda_{vdwAex}$ is smaller than 1 for an intermediate state, $\lambda_{elecAex}$ is 0 for that intermediate state; and if $A_a$ and $A_b$ are not valence-bonded to each other in the reference state and valence-bonded in the target state, and the nonbonded interactions between $A_i$ and $A_j$ are not excluded in the reference state but excluded in the target state, varying each of $\lambda_{elecBex}$ and $\lambda_{vdwBex}$ according to a schedule for each of the intermediate states along the transformation from the reference state to the target state such that when $\lambda_{vdwAex}$ is smaller than 1 for an intermediate state, $\lambda_{elecAex}$ is 0 for that intermediate state.

In some embodiments of the method, performing molecular simulations for all of the states further includes:

(a) computing nonbonded electrostatic 1-4 pair interactions and van der Waals 1-4 pair interactions, using applicable parameters for electrostatic 1-4 pair interactions and van der Waals 1-4 pair interactions of a force field, between two atoms $A_i$ and $A_j$ which together with another two intervening atoms forms a bonded dihedral angle interaction in either the reference state or the target state;

(b) if $A_a$ and $A_b$ are valence-bonded to each other in the reference state and not valence-bonded in the target state:

if the nonbonded 1-4 pair interactions between $A_i$ and $A_j$ are included in the reference state but not included in the target state, multiplying the nonbonded electrostatic 1-4 pair interactions and van der Waals 1-4 pair interactions between $A_i$ and $A_j$ obtained in (a) by coupling parameters $\lambda_{elecA14}$ and $\lambda_{vdwA14}$, respectively, wherein both of $\lambda_{elecA14}$ and $\lambda_{vdwA14}$ are 1 at the reference state, 0 at the target state, and varied from 1 to 0 at each intermediate state along the transformation from the reference state to the target state, and if the nonbonded 1-4 pair interactions between $A_i$ and $A_j$ are not included in the reference state but included in the target state, multiplying the nonbonded electrostatic 1-4 pair interactions and van der Waals 1-4 pair interactions between $A_i$ and $A_j$ obtained in (a) by coupling parameters $\lambda_{elecB14}$ and $\lambda_{vdwB14}$, respectively, wherein both of $\lambda_{elecB14}$ and $\lambda_{vdwB14}$ are 0 at the reference state, 1 at the target state, and varied from 1 to 0 at each intermediate state along the transformation from the reference state to the target state, and if $A_a$ and $A_b$ are not valence-bonded to each other in the reference state and valence-bonded in the target state:

if the nonbonded 1-4 pair interactions between $A_i$ and $A_j$ are not included in the reference state but included in the target state, multiplying the nonbonded electrostatic 1-4 pair interactions and van der Waals 1-4 pair interactions between $A_i$ and $A_j$ obtained in (a) by coupling parameters $\lambda_{elecB14}$ and $\lambda_{vdwB14}$, respectively, wherein both of $\lambda_{elecB14}$ and $\lambda_{vdwB14}$ are 0 at the reference state, 1 at the target state, and varied from 0 to 1 at each intermediate state along the transformation from the reference state to the target state, and if the nonbonded 1-4 pair interactions between $A_i$ and $A_j$ are included in the reference state but not included in the target state, multiplying the nonbonded electrostatic 1-4 pair interactions and van der Waals 1-4 pair interactions between $A_i$ and $A_j$ obtained in (a) by the coupling parameters $\lambda_{elecA14}$ and $\lambda_{vdwA14}$, respectively, wherein both of $\lambda_{elecA14}$ and $\lambda_{vdwA14}$ are 1 at the reference state, 0 at the target state, and varied from 1 to 0 at each intermediate state along the transformation from the reference state to the target state; and (c) including the calculated electrostatic 1-4 pair interactions and van der Waals 1-4 pair interactions obtained in (b) into the total energy of the simulation step of the corresponding system state.

In some embodiments of the method, performing molecular simulations for all of the states further includes:

(a) if $A_a$ and $A_b$ are valence-bonded to each other in the reference state and not valence-bonded in the target state, if the nonbonded 1-4 pair interactions between $A_i$ and $A_j$ are included in the reference state but not included in the target state, varying each of $\lambda_{elecA14}$ and $\lambda_{vdwA14}$ according to a schedule for each of the intermediate states along the transformation from the reference state to the target state such that when $\lambda_{vdwA14}$ is smaller than 1 for an intermediate state, $\lambda_{elecA14}$ is 0 for that intermediate state;

if the nonbonded 1-4 pair interactions between $A_i$ and $A_j$ are not included in the reference state but included in the target state, varying each of $\lambda_{elecB14}$ and $\lambda_{vdwB14}$ according to a schedule for each of the intermediate states along the transformation from the reference state to the target state such that when $\lambda_{vdwB14}$ is smaller than 1 for an intermediate state, $\lambda_{elecB14}$ is 0 for that intermediate state (b) if $A_a$ and $A_b$ are not valence-bonded to each other in the reference state and valence-bonded in the target state, if the nonbonded 1-4 pair interactions between $A_i$ and $A_j$ are not included in the reference state but included in the target state, varying each of $\lambda_{elecB14}$ and $\lambda_{vdwB14}$ according to a schedule for each of the intermediate states along the transformation from the reference state to the target state such that when $\lambda_{vdwB14}$ is smaller than 1 for an intermediate state, $\lambda_{elecB14}$ is 0 for that intermediate state, if the nonbonded 1-4 pair interactions between $A_i$ and $A_j$ are included in the reference state but not included in the target state, varying each of $\lambda_{elecA14}$ and $\lambda_{vdwA14}$ according to a schedule for each of the intermediate states along the transformation from the reference state to the target state such that when $\lambda_{vdwA14}$ is smaller than 1 for an intermediate state, $\lambda_{elecA14}$ is 0 for that intermediate state;

In some embodiments of the method, computing van der Waals interactions can include using a soft-core LJ interaction potential.

In some embodiments of the method, either the reference state or the target state includes a molecule having a ring structure in which the atoms $A_a$ and $A_b$ are bonded to each other and form a part of the ring structure.

In some embodiments of the method, calculating the free energy difference between the reference state and the target state comprises performing an analysis of the ensemble of micro-states obtained at the target state, the reference state, and the intermediate states by way of a determination and analysis of the work associated with the variation of coupling parameter $\lambda$.

In some embodiments of the method, calculating the free energy difference between the reference state and the target state comprises performing an analysis of the ensemble of micro-states obtained at the target state, the reference state, and the intermediate states by way of an analysis of the differences in a thermodynamic property of a suitable ensemble of the micro-states obtained at the target state, the reference state, and the intermediate states as the coupling parameter $\lambda$ is instantaneously varied for the selected ensemble of micro-states. Performing the analysis of the differences in the thermodynamic property comprises applying an estimator selected from BAR, MBAR, WHAM, Zwanzig average estimators, or one of an FEP-family estimators. The ensemble can be, for example, an NVT ensemble, a NPT ensemble, a NVE ensemble, and a µVT ensemble.

In some embodiments of the method, calculating the free energy difference between the reference state and the target state comprises performing a thermodynamic integration analysis of the derivative of a thermodynamic property of a suitable ensemble of micro-states obtained for the target state, the reference state, and the intermediate states with respect of the coupling parameter $\lambda$. The ensemble can be, for example, an NVT ensemble, a NPT ensemble, a NVE ensemble, and a µVT ensemble.

The invention also provides an apparatus including one or more processors, a memory operably coupled to the one or more processors comprising instructions executable by the processors, the one or more processors being operable when executing the instructions to perform the various embodiments of the method as described herein. The invention further provides non-transitory computer readable media storing the instructions which when executed by one or more processors, carry out the various embodiments of the method as described herein.

Other features and advantages of the invention are apparent from the following description, and from the claims.

BRIEF DESCRIPTION OF THE DRAWINGS

The present invention will be better understood by reference to the accompanying drawings, wherein:

FIGS. 1a-1c are diagrams showing illustrative ring-closing transformations between a reference system state to a target system state according to some embodiments of the present invention;

FIG. 2 depicts plots of a soft bond potential as a function of inter-atom distance between the two atoms involved in a bond formation or breaking transformation at different values of the coupling parameter $\lambda$ according to some embodiments of the present invention;

DETAILED DESCRIPTION

The present application discloses computer-implemented methods and systems for computing free energy difference between a reference system state and a target system state. In particular, to address the issues in determining free energy difference arising from bond breaking in a ring structure that transforms a ring structure to a linear structure and bond formation that transforms a linear structure into a ring structure (each of which is further discussed below), the methods and systems disclosed in the present application utilize a functional form for bond stretching that allows a rigorous connection to the harmonic bond functional form to be maintained at any points in the alchemical transformation for calculating the free energy difference. Accordingly, the methods and systems of the present application can advantageously improve numerical stability and accuracy of the free energy calculations. However, it is to be recognized that the general principles of the free energy calculations using such modified bond stretching potentials disclosed herein can be applied generally in any bond formation and breaking situations, and not limited to ring closing or ring opening.

Figure 1A:
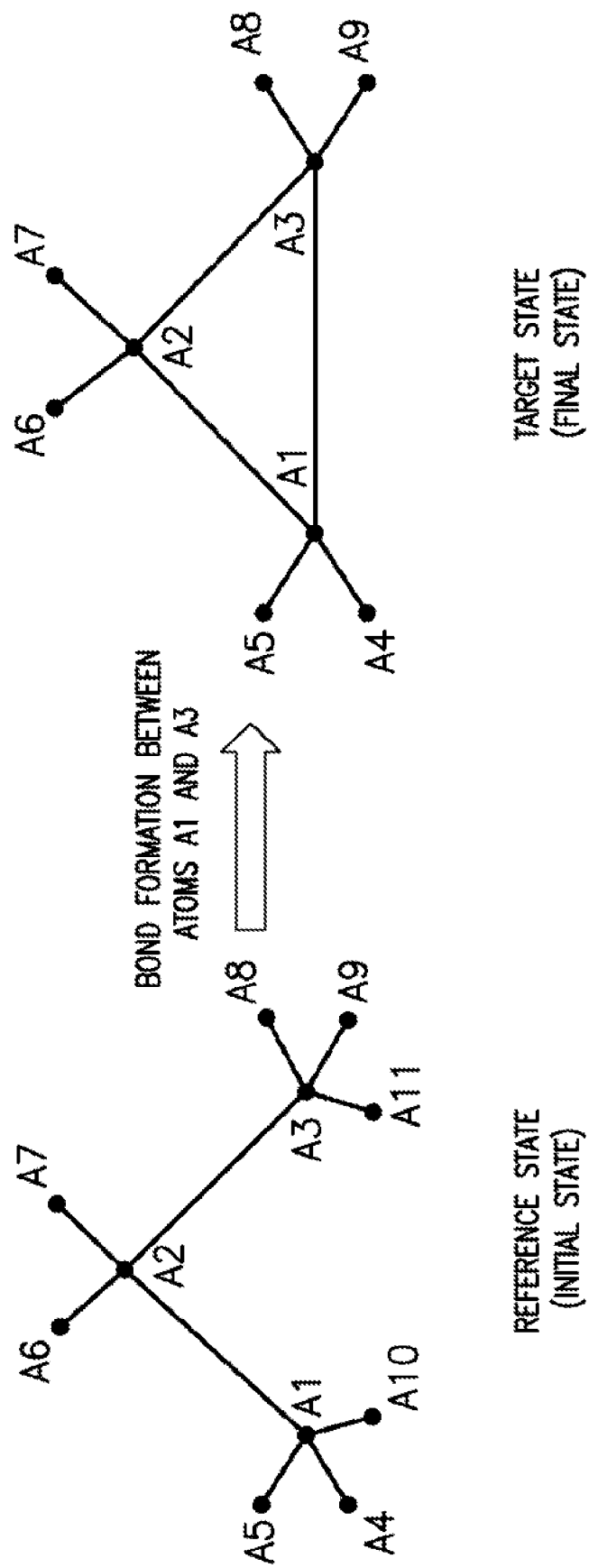
Figure 1B:
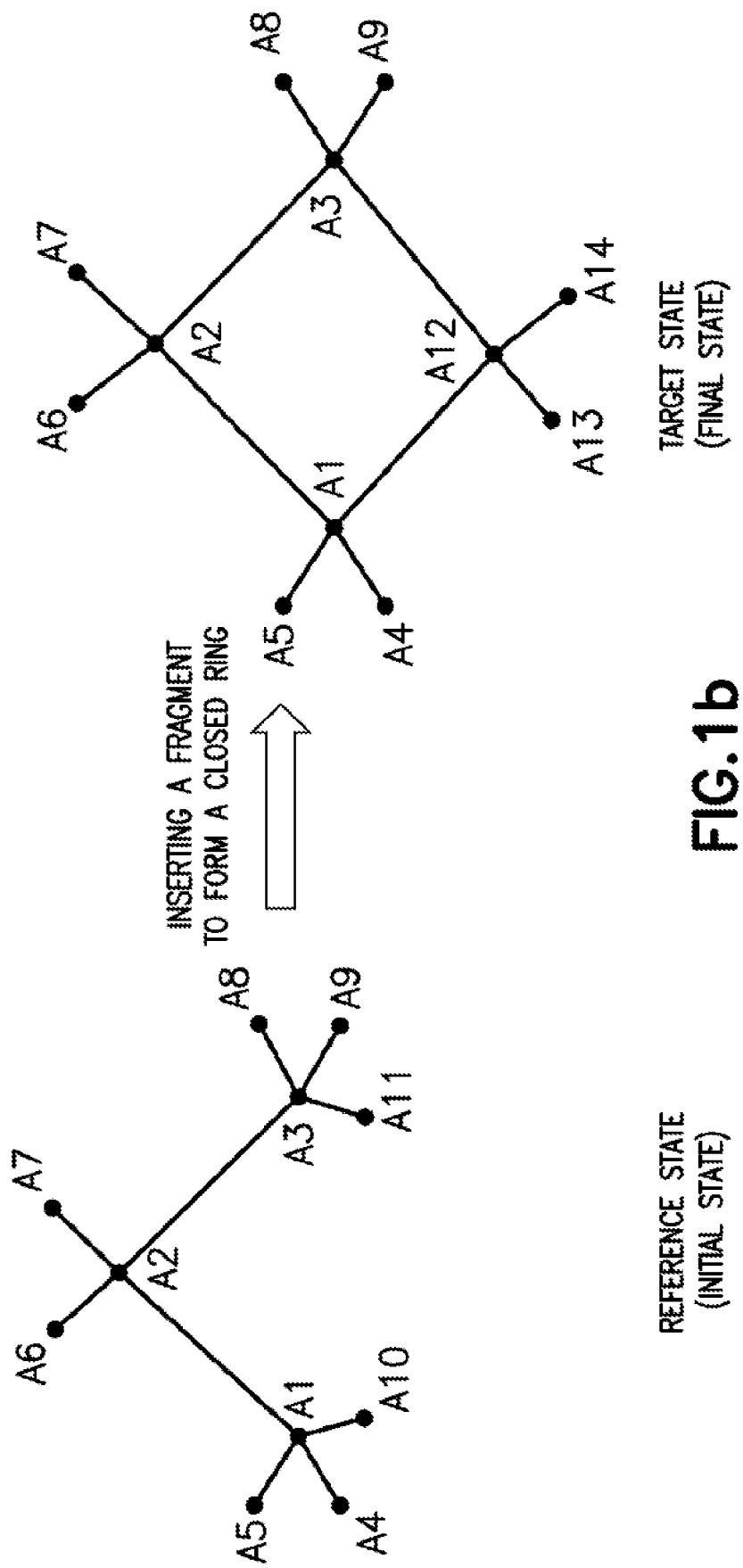

As with traditional free energy difference calculations, the atoms in the system can be categorized into different groups for evaluating the system energy in different system states. The reference state and target state both include a common set of atoms $P_{AB}$. The reference state further includes a set of atoms $P_A$, and the target state further includes a set of atoms $P_B$. The set of atoms $P_A$ are present only in the reference state and not in the target state, and the set of atoms $P_B$ are present only in the target state and not the reference state. In a ring formation scenario, $P_A$ can be the atoms connected to the two terminal atoms to form a bond. During the course of the transformation, the atoms in $P_A$ and in $P_B$ interact with other atoms within their own set as well as with those in $P_{AB}$, but the atoms in $P_A$ do not interact with any atoms in $P_B$, or vice versa. For example, for a molecule having a structure shown in FIG. 1a, where a bond is about to be formed between two atoms $A_1$ and $A_2$, $P_{AB}=\{A_1, A_2, A_3, A_4, A_5, A_6, A_7, A_8, A_9\}$ (the atoms are shown as having valence of 4 for purpose of illustration only; it is understood that other atoms or groups can be represented in this structure), $P_A=\{A_{10}, A_{11}\}$, and $P_B=\emptyset$. By way of another example, for a molecule having a backbone structure $A_1$-$A_3$-$A_2$ shown in FIG. 1b, where a molecular fragment including $A_{12}, A_{13}, A_{14}$ is to be inserted between $A_1$ and $A_3$ to form two bonds $A_1$-$A_{12}$ and $A_3$-$A_{12}$, $P_{AB}=\{A_1, A_2, A_3, A_4, A_5, A_6, A_7, A_8, A_9\}$; $P_A=(A_{10}, A_{11})$, and $P_B=\{A_{12}, A_{13}, A_{14}\}$. In the latter example, the insertion of the fragment to form the two bonds can be considered as taking two steps, the first being a linear growth of the chain $A_3$-$A_2$-$A_1$ on $A_1$ (or $A_3$) by the fragment containing $A_{12}$, and the second step being the closure of the ring between $A_{12}$-$A_3$ (or $A_{12}$-$A_1$). In another example as illustrated in FIG. 1c, where a molecule having a closed 4-membered ring structure is alchemically transformed into a 5-membered ring structure, $P_{AB}=\{A_1, A_2, A_3, A_4, A_5, A_6, A_7, A_8, A_9, A_{10}, A_{11}, A_{12}\}$, $P_A=\emptyset$, $P_B=\{A_{13}, A_{14}, A_{15}\}$.

As described herein, the coupling Hamiltonian $\mathcal{H}(\lambda)$ for alchemical transformation involving ring opening and closing can generally include the following terms, $\mathcal{H}_{bs}(\lambda_{bs})$, $\mathcal{H}_{ba}(\lambda_{ba})$, $\mathcal{H}_{bd}(\lambda_{bd})$ and $\mathcal{H}_{nb}(\lambda_{nb})$, corresponding to the bonded stretch terms, the bonded angle terms, the bonded dihedral angle terms, and the nonbonded exclusion and 1-4 pair interaction terms respectively. To simplify the discussion, in the following the case where a valence bond between two ring atoms is being formed (i.e., the transformation from the reference state to the target state involves ring closing) is described in detail.

As an initial step, the topology of the system is provided, including the bonded connections between the atoms in the system and the relative spatial arrangements of the atoms forming each of $P_{AB}$, $P_A$, and $P_B$.

One or more, e.g., a plurality of intermediate states between the reference state and the target state can be determined along a path defined by different values of the coupling parameter $\lambda$, where the increments of $\lambda$ in value move the system from the reference state to the target state. While $\lambda$ can be a scalar variable that varies from 0 to 1, in some embodiments of the present invention, such as those further discussed below, $\lambda$ can be a vector containing different components for different types of interactions within the system. Computer molecular simulations, such as, but not limited to, molecular dynamics or Monte Carlo simulations, can be performed to obtain ensembles of the micro-states for the reference state, the target state, and each of the intermediate states. The $\lambda$ values of the intermediate states can be chosen by known techniques such that between each neighboring $\lambda$ windows on the "reaction pathway" from the reference state to the target state there is substantial overlap between the micro-states in the successive $\lambda$ windows that are sampled by the molecular simulations.

In performing molecular simulations for all these states, the bonded stretch interaction energy between the two atoms $A_a$ and $A_b$ that are to form a bond (e.g., $A_1$ and $A_3$ in FIG. 1a) can be defined by a soft bond potential which is modulated by $\lambda$ (or the bond stretch component thereof). When $\lambda=0$ ($A_a$ and $A_b$ are completely nonbonded in the reference state), the soft bond potential is a flat potential for all distances r between $A_a$ and $A_b$. When $0<\lambda<1$, (the bond between $A_a$ and $A_b$ is being "partially formed" in the alchemical transformation), the soft bond potential levels off to a flat potential when $r \to \infty$, i.e., the partial derivative of the potential with respect to the distance r between $A_a$ and $A_b$ is zero when $r \to \infty$. When $\lambda=1$ ($A_a$ and $A_b$ are fully valence bonded in the target state), the soft bond potential reverts to a harmonic potential. Further, the potential energy function for the bond stretch term does not have any singular regions for all values of the bonded stretch component, $\lambda_{sbs}$, of the coupling parameter $\lambda$ within [0,1] and for all values of the distance r between Aa and Ab. The details of developing the soft bond potential and some properties of the soft bond potential are provided below.

In popular molecular mechanics force fields, such as OPLS, CHARMM, and AMBER, the bonded stretch interactions between two atoms are modeled by a harmonic bond of the following form:

$$U_{bs}(\lambda,r) = \tfrac{1}{2} k (r-r_0)^2 \qquad (5)$$

where k is the "force constant" or "Hookean constant" which defines the strength (or rigidity) of the bond of the force field used, r is the instantaneous distance between the two atoms and $r_0$ is the equilibrium distance between the two atoms. In conventional method of linear scaling of the coupling parameter between the Hamiltonians of the reference state and the target state, the bonded stretch term has the following form in the coupling Hamiltonian:

$$U_{bs}(\lambda, r) = \frac{1}{2}\lambda k(r-r_0)^2 \tag{6}$$

Therefore, $$\frac{\partial F(\lambda)}{\partial \lambda} = \left\langle \frac{\partial U_{bs}(\lambda, r)}{\partial \lambda} \right\rangle_\lambda = \left\langle \frac{1}{2}k(r-r_0)^2 \right\rangle_\lambda. \tag{7}$$

The integrand in the above equation approaches infinity when r is very large. In the limit when $\lambda$ approaches 0, there is no bonded stretch interaction between the two atoms, and the distance between the two atoms can be very large, leading to singularity and numerical instability problem in the calculation of the above integral. In practice, the distance between the two atoms is limited by the size of the simulation box (a three-dimensional volume or unit cell in which the simulation is conducted and boundary conditions, such as periodic boundary conditions, can be applied), the singularity problem can be avoided. However, since the integrand in the above equation is unbounded, it can still cause numerical instability and inaccuracy problems in the free energy calculations.

Additionally, using the above conventional coupling Hamiltonian functional form, the potential is undefined for $\lambda=0$ when r approaches infinity. The limiting value depends on how $\lambda$ approaches 0 and how r approaches infinity, i.e.:

$$\lim_{r\to\infty}\lim_{\lambda\to 0} U_{bs}(\lambda, r) = \lim_{r\to\infty}\lim_{\lambda\to 0} \frac{1}{2}\lambda k(r-r_0)^2 \text{ diverges} \tag{8}$$

In order to obtain a pathway that allows stable and efficient simulations from which reliable free energies involving the annihilation and/or formation of a bond between two atoms can be determined, the present inventors have discovered the following coupling potential (referred to herein as the soft bond potential) to connect the two physical systems where the harmonic interactions between the two atoms are fully turned on and off when the coupling parameter $\lambda$ changes between 0 and 1:

$$U_{sbs}(r, \lambda) = \frac{1}{2}kf(\lambda)(r-r_0)^2 \frac{1}{1+g(\lambda)\alpha(k,\lambda)(r-r_0)^2} \tag{9}$$

where the functions $f$, $g$ and $\alpha$ are each continuous functions and simultaneously satisfy the following conditions: $f(\lambda=0)=0$; $f(\lambda=1)=1$; $g(\lambda=0)=1$; $g(\lambda=1)=0$; $\alpha(k,\lambda<1)>0$. It is noted that for all the discussions herein regarding the soft bond potential for the bonded stretch interactions, $\lambda$ as used in the equations (from Equation 9 and onwards) refers to the bonded stretch component, $\lambda_{sbs}$, of the coupling parameter $\lambda$.

In particular example of the soft bond potential described by Eq. 9, $f(\lambda)=\lambda$, $g(\lambda)=1-\lambda$ and $\alpha(k,\lambda)=\alpha=$const (a constant number), i.e., the soft bond potential takes the following form:

$$U_{sbs}(r, \lambda) = \frac{1}{2}\lambda k(r-r_0)^2 \frac{1}{1+\alpha(1-\lambda)(r-r_0)^2} \tag{10}$$

It can be seen that the soft bond interaction of Eq. 10 correctly recovers the two physical end states when $\lambda=0$ and $\lambda=1$:

$$U_{sbs}(r, \lambda=1) = \frac{1}{2}k(r-r_0)^2 \tag{11}$$

$$U_{sbs}(r, \lambda=0) = 0$$

$$U_{sbs}(r \to \infty, \lambda) = \frac{k\lambda}{2\alpha(1-\lambda)} \text{ when } \lambda \neq 1$$

The introduction of $\alpha(1-\lambda)(r-r_0)^2$ in the denominator of Eq. 10 changes the harmonic interaction into a soft bond interaction (the interaction is bounded when r approaches infinity) when $\lambda$ is smaller than 1, and at $\lambda=1$ (the bond is formed) the function has the exact harmonic potential form.

The above functional form removes the singularity and numerical instability problems associated with the conventional harmonic potentials. In the following, some properties of the soft bond interaction functional form as exemplified by Eq. 10 are discussed.

Property 1:

The soft bond interaction functional form does not have any singular regions for all values of $\lambda$ between 0 and 1 and for all values of r. From the above description, i.e.:

$$U_{sbs}(r, \lambda=1) = \frac{1}{2}k(r-r_0)^2 \tag{12}$$

$$U_{sbs}(r, \lambda=0) = 0$$

$$U_{sbs}(r, \lambda) = \frac{1}{2}\lambda k(r-r_0)^2 \frac{1}{1+\alpha(1-\lambda)(r-r_0)^2} \text{ for } \lambda \in (0, 1)$$

The soft bond potential for a model system with the force constant k=20 kcal·mol$^{-1}$·Å$^{-2}$ and the soft bond parameter $\alpha=1$ at different values of $\lambda$ are given in FIG. 2. It can be seen clearly that the potential is continuous for all values of $\lambda$ and r. It changes slowly from a harmonic potential at $\lambda=1$ to a soft bond potential at intermediate values of $\lambda$, and goes to 0 at $\lambda=0$.

Property 2:

$$\frac{\partial F_{sbs}(\lambda)}{\partial \lambda} = \left\langle \frac{\partial U_{sbs}(\lambda)}{\partial \lambda} \right\rangle_\lambda = \left\langle \frac{1}{2}k(r-r_0)^2 \frac{1+\alpha(r-r_0)^2}{(1+(1-\lambda)\alpha(r-r_0)^2)^2} \right\rangle_\lambda \tag{13}$$

As discussed in the above section, it is $$\frac{\partial F(\lambda)}{\partial \lambda}$$

which determines the numerical stability and accuracy of the free energy calculations. In the above formulation, when $\lambda \in [0,1)$, the thermodynamic property to be averaged in the rightmost bracket in Eq. 13 is continuous and bounded for all values of r. When $\lambda=1$, the soft bond potential recovers the harmonic potential, so only phase space regions where r is close to $r_0$ are sampled and taken into the ensemble average. In the phase space regions where r is close to $r_0$, the integrand in Eq. 13 is also bounded. Therefore, the quantity in the bracket of Eq. 13 is bounded for all values of $\lambda$ between 0 and 1. Since $$\frac{\partial F(\lambda)}{\partial \lambda}$$

does not have any singular region for all values of $\lambda$ between 0 and 1, accurate and reliable free energy results can be obtained using the above soft bond interaction functional form.

Figure 3:
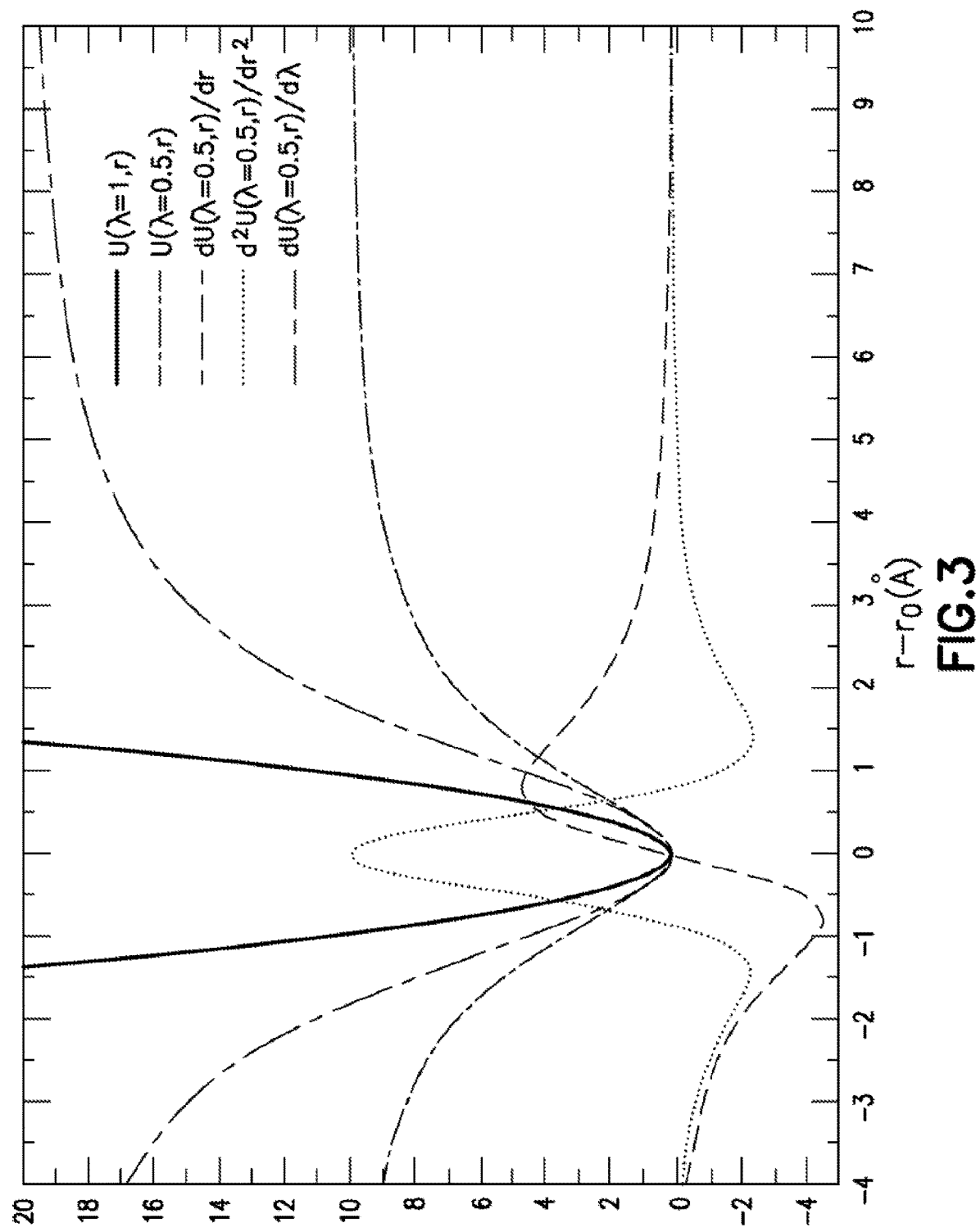
FIG. 3 depicts plots of a soft bond potential as a function of inter-atom distance between the two atoms involved in a bond formation or breaking transformation at different values of the coupling parameter $\lambda$, as well as the derivative of the potential with respect to the coupling parameter $\lambda$, and the first and second derivative of the potential with respect to the inter-particle distance according to some embodiments of the present invention.

As an example, the derivative of the soft bond potential of Eq. 10 with respect to the coupling parameter $\lambda$ at $\lambda=0.5$ for a model system with force constant k=20 kcal·mol$^{-1}$·Å$^{-2}$ and the soft bond parameter $\alpha=1$ is plotted in FIG. 3. It can be seen that $$\frac{\partial F(\lambda)}{\partial \lambda}$$

does not have any singular region for all values of $\lambda$ and r, allowing reliable and accurate free energy calculations.
Property 3:

$$\frac{\partial U_{sbs}(\lambda, r)}{\partial r} = k\lambda \frac{r - r_0}{(1 + (1 - \lambda)\alpha(r - r_0)^2)^2} \quad (14)$$

$$\frac{\partial^2 U_{sbs}(\lambda, r)}{\partial r^2} = k\lambda \frac{1 - 3(1 - \lambda)\alpha(r - r_0)^2}{(1 + (1 - \lambda)\alpha(r - r_0)^2)^3}$$

Both the first derivative and the second derivative of the soft bond potential of Eq. 10 with respect to the inter-particle (or inter-atom) distance r are continuous and bounded for all values of $\lambda \in [0,1]$ and they are short ranged and approaching 0 when $r \to \infty$. When $\lambda=1$, the soft bond potential reverts to the harmonic potential, and only phase space regions where r is close to $r_0$ are sampled in the molecular simulations. Thus the first and the second derivatives of the potential with respect to the inter-particle distance r are also continuous and bounded in the physically accessible phase space regions when $\lambda=1$. Therefore, the forces and acceleration on the atoms are always continuous and bounded for all values of $\lambda$ between 0 and 1, allowing stable molecular dynamics simulations to be performed for all values of $\lambda$. As an example, the first and second derivative of the soft bond potential with respect to the inter-particle distance r at $\lambda=0.5$ for a model system with force constant k=20 kcal·mol$^{-1}$·Å$^{-2}$ and the soft bond parameter $\alpha=1$ are plotted in FIG. 3. It can be seen that those derivatives are continuous over the whole space, allowing stable molecular dynamics simulations.

It is clear from the above description that the soft bond potential removes the singularity and numerical instability problems associated with the traditional methods, and it allows stable molecular dynamics simulations and more convergent Monte Carlo to be performed for all system states, including the reference system state, the intermediate system states, and the target system state. Using the soft bond potential described herein, the free energy difference between the reference system state and the target system state involving breaking and form valance bond can be accurately and reliable calculated. The free energy calculations utilizing such a soft bond potential are particularly advantageous for alchemical transformations involving ring opening, ring closing, or ring rearrangement, where the computational efficiency and convergence of the free energy calculations can be significantly improved over the conventional methods.

As described in above section, in the conventional coupling Hamiltonian, the limit does not exist for the initial state where $\lambda=0$ when r approaches infinity, while in the soft bond potential the limit exists for all values of r. The conventional coupling Hamiltonian is a special case of the soft bond potential where $\alpha=0$. While the conventional coupling Hamiltonian and the soft bond potential reach the same end state when $\lambda=1$, the initial states when $\lambda=0$ are different depending on the value of the soft bond parameter $\alpha$. In the following, it is shown that the free energy of the initial state does not depend on the soft bond parameter $\alpha$.

Consider a Hamiltonian with the following potential energy term (i.e., Eq. 10 where $\lambda=0$):

$$U(r, \alpha, \lambda) = \frac{1}{2}k\lambda(r - r_0)^2 \frac{1}{1 + \alpha(r - r_0)^2} \quad (15)$$

When $\alpha=0$, it becomes the conventional harmonic potential, and when $\alpha \neq 0$ it becomes the soft bond potential. We need to prove that $$F(\alpha=0, \lambda=0) = F(\alpha=\alpha'>0, \lambda=0) \quad (16)$$

Note that $$F(\alpha = \alpha' > 0, \lambda = 0) - F(\alpha = 0, \lambda = 0) = \int_0^{\alpha'} d\alpha \lim_{\lambda \to 0} \frac{\partial F(\alpha, \lambda)}{\partial \alpha} \quad (17)$$

where $$\frac{\partial F(\alpha, \lambda)}{\partial \alpha} = \left\langle \frac{\partial U(r, \alpha, \lambda)}{\partial \alpha} \right\rangle_\alpha = \quad (18)$$

$$\left\langle \frac{k\lambda(r-r_0)^4}{2(1+\alpha(r-r_0)^2)^2} \right\rangle_\alpha = \lambda \left\langle \frac{k(r-r_0)^2}{2(1+\alpha(r-r_0)^2)^2} \right\rangle_\alpha = \lambda I(\alpha)$$

The ensemble average $I(\alpha)$ is a finite number since $$I(\alpha) = \left\langle \frac{k(r-r_0)^4}{2(1+\alpha(r-r_0)^2)^2} \right\rangle_\alpha = \quad (19)$$

$$\int_0^{r_{max}} dr \frac{k(r-r_0)^4}{2(1+\alpha(r-r_0)^2)^2} \frac{\exp(-\beta U(r,\alpha,\lambda))}{\int_0^{r_{max}} dr \exp(-\beta U(r,\alpha,\lambda))} \le$$

$$\int_0^{r_{max}} dr \, k(r-r_0)^4 \frac{1}{\exp(-\beta U(r_{max},\alpha,\lambda))V} \le$$

$$\frac{kr_{max}^4}{\exp(-\beta U(r_{max},\alpha,\lambda))V}$$

Therefore, $$\lim_{\lambda \to 0} \frac{\partial F(\alpha, \lambda)}{\partial \alpha} = \lim_{\lambda \to 0} \lambda I(\alpha) = 0 \quad (20)$$

$$F(\alpha = \alpha' > 0, \lambda = 0) - F(\alpha = 0, \lambda = 0) = 0$$

In view of the above, the initial state for the conventional coupling Hamiltonian and soft bond potential when $\lambda=0$ have the same free energy.

In free energy calculations, the convergence of the free energy can be affected by the overlap of phase space regions between neighboring or successive $\lambda$ windows. Empirically, a suitable path from the initial state to the final state can be achieved when the change of the free energy as a function of $\lambda$ is continuous and smooth for all values of $\lambda$, i.e.:

$$\frac{\partial F_{sbs}(\lambda)}{\partial \lambda} = \left\langle \frac{\partial U_{sbs}(\lambda)}{\partial \lambda} \right\rangle_\lambda = \left\langle \frac{1}{2}k(r-r_0)^2 \frac{1+\alpha(r-r_0)^2}{(1+(1-\lambda)\alpha(r-r_0)^2)^2} \right\rangle_\lambda \approx const \quad (21)$$

Thus, in preferred embodiments, the value of the soft bond parameter $\alpha$ can be obtained when Eq. 21 is satisfied.

As mentioned above, in ring opening and closing free energy calculations, in addition to the bonded stretch interactions, there can be other interaction energy terms which are different in the initial and final states, including the bonded angle terms, the bonded dihedral angle terms, and the nonbonded interactions. These different types of interactions can be treated differently during the transformation process. As described herein, in some embodiments, the coupling parameter $\lambda$ can take a vector form which includes components for different types of interactions. For example, the coupling vector $\lambda$ can include the following components for interactions affected by the formation (or the breaking) of the valence bond between the reference state and the target state: a component $\lambda_{sbs}$ for bonded stretch energy term; a component $\lambda_{ba}$ for the bonded angle energy term; a component $\lambda_{bd}$ for bonded dihedral angle energy term; components $\lambda_{vdw}$ and $\lambda_{elec}$ for the van de Waals and electrostatic energy terms of the nonbonded exclusion and 1-4 pair interaction, respectively. The coupling vector $\lambda$ can further include components $\lambda_{other}$ for other interactions not affected by the formation and/or breaking of the valence bond between the reference state and the target state. Each component of the coupling vector $\lambda$ belongs to [0, 1]. During the course of the alchemical transformation from the reference state to the target state, the interactions unique in the reference state can be turned off according to a first set of schedules for different $\lambda$ components, and the interactions unique in the target state can be turned on according to a second set of schedules for different $\lambda$ components, as will be further described below.

In popular molecular mechanics force fields, the bonded angle and bonded dihedral angle interactions usually have the following potential energy form:

$$U_{ba}(\theta) = k_\theta(\theta - \theta_0)^2 \quad (22)$$

$$U_{bd}(\phi) = k_\phi \sum_n f(\cos(n\phi)) \quad (23)$$

where $\theta$ is the bond angle, $\theta_0$ is the equilibrium bond angle, $k_\theta$ is the angle force constant (both $\theta_0$ and $k_\theta$ depend on the atoms forming the bond angle); $\phi$ is the dihedral angle, $k_\phi$ is the dihedral angle force constant (which depends on the atoms forming the dihedrals). With the opening or closing of a ring, the bonded angle and dihedral angle terms that are affected by the breaking or forming of the bond can be modulated by components $\lambda_{ba}$ and $\lambda_{bd}$ of the coupling parameter $\lambda$, respectively. Although the bonded angle and dihedral interaction terms are bounded for all $\lambda$ values, the absolute values of these terms can be very large if the molecule is in a very twisted geometry. To improve the accuracy of the free energy calculation, in some embodiments, the bonded stretch interaction can be first turned on to a significant degree (e.g., $\lambda_{sbs}$=0.5) before turning on the bonded angle and bonded dihedral angle interaction (during bond formation). In this way, the bonded stretch interaction will steer the molecule clear from a severely twisted geometry, improving the inaccuracy problem caused by the bonded angle and bonded dihedral angle interactions in the free energy calculations.

The nonbonded electrostatic and van der Waals interactions between two atoms are usually modeled by the following potential energy form in popular molecular mechanics force fields:

$$U_{elec}(r) = C\frac{q_1 q_2}{r} \quad (24)$$

$$U_{vdw}(r) = 4\varepsilon\left[\left(\frac{\sigma}{r}\right)^{12} - \left(\frac{\sigma}{r}\right)^6\right] \quad (25)$$

where in Eqs. 24 and 25, r is the inter-atom distance, $q_1$ and $q_2$ are the charges of the two atoms, C is a constant, $\varepsilon$ is the depth of the potential well of $U_{vdw}(r)$, and $\sigma$ is the finite distance at which the inter-atom potential $U_{vdw}(r)$ is zero.

Many force fields, including OPLS, CHARM, AMBER, exclude or modify the nonbonded interactions between atoms separated by one, two, or three bonds. In particular, when two atoms are separated by three bonds (e.g., the two atoms $A_1$ and $A_8$ shown in FIG. 1a), the conventional non-bonded electrostatic and van der Waals interactions as described in Eq. 24 between the two atoms are not calculated (i.e., excluded); instead, they are substituted by electrostatic 1-4 pair and van der Waals 1-4 pair interactions.

With the opening or closing of a ring, the nonbonded electrostatic and van der Waals interactions for atoms that span the bond that is broken or forming can be modulated for by components $\lambda_{elec}$ and $\lambda_{vdw}$, respectively, which will be further discussed below. As used herein, in some embodiments of the invention, the van der Waals and/or the electrostatic interaction can be described by a soft-core Lennard Jones (LJ) and/or soft-core Coulomb potential that keeps pairwise interaction energies finite for all configurations. By way of example, a soft-core LJ potential may take the following functional form:

$$U_{LJ}(r, \lambda) = 4\varepsilon\lambda\left(\frac{1}{\left(\alpha_{LJ}(1-\lambda)^n + (r/\sigma)^6\right)^2} - \frac{1}{\alpha_{LJ}(1-\lambda)^n + (r/\sigma)^6}\right) \quad (26)$$

where it $\alpha_{LJ}$ is the soft core parameter, $\varepsilon$ and $\sigma$ are the standard Lennard Jones interaction parameters, n is the order parameter which usually takes values between 1 and 6. See Beutler et al., "Avoiding singularities and numerical instabilities in free energy calculations based on molecular simulations," Chem. Phys. Lett., 222 (1994) 529-539, the disclosure of which is incorporated by reference herein. The soft-core LJ interaction recovers the standard Lennard Jones interactions when $\lambda$=1 and it becomes 0 when $\lambda$=0.

In some embodiments, for ring opening and closing free energy calculations, a $\lambda$ schedule for all the system states can be used to treat the bonded stretch, bonded angle, bonded dihedral angle, nonbonded exclusion and 1-4 pair interactions, that are affected by the formation and/or annihilation of a bond that results in the opening or the closing of a ring structure. The coupling parameter λ for those interactions affected by the bond formation or breaking may include seven components for bond breaking transformation and seven components for bond formation transformation from the reference state to the target state.

The seven components of the coupling parameter λ applicable for the bond breaking transformation include the following terms: $\lambda_{sbsA}$, which modulates the bonded stretch interactions, respectively, that are present in the initial state (the bond is present and yet to be broken) but not in the final state (the bond is broken); $\lambda_{baA}$ and $\lambda_{bdA}$, which modulate the bonded angle and bonded dihedral angle interactions that are present in the initial state but not in the final state; $\lambda_{elecA_{ex}}$ and $\lambda_{vdwA_{ex}}$, which modulate the nonbonded electrostatic interactions and van der Waals interactions present in the final state but excluded (nonbonded exclusions) in the initial state due to the breaking of a bond present in the initial state during the transformation from the initial state to the final state, and $\lambda_{elecA_{14}}$ and $\lambda_{vdwA_{14}}$ which modulate the electrostatic 1-4 pair and van der Waals 1-4 pair interactions present in the initial state but not included in the final state due to the breaking or formation of the bond during the transformation from the initial state to the final state.

Similarly, the seven components for bond formation transformation include the following terms: $\lambda_{sbsB}$, which modulates the bonded stretch interactions that are present in the final state (the bond is formed) but not in the initial state (the bond is yet to be formed), $\lambda_{baB}$ and $\lambda_{bdB}$, which modulate the bonded angle and bonded dihedral angle interactions that are present in the final state but not in the initial state, respectively, $\lambda_{elecB_{ex}}$ and $\lambda_{vdwB_{ex}}$, which modulate the nonbonded electrostatic and van der Waals interactions present in the initial state but excluded in the final state due to the formation of a bond in the final state, and $\lambda_{elecB_{14}}$ and $\lambda_{vdwB_{14}}$, which modulate the electrostatic 1-4 pair and van der Waals 1-4 pair interactions present in the final state but excluded in the initial state due to the formation or breaking of the bond during the transformation from the initial state to the final state.

As used herein, the term "modulate" when used in connection with a component of the coupling parameter λ means that the interaction energy for that particular component is calculated using parameters of a conventional force field and the corresponding component coupling parameter. To be specific, for bonded stretch interaction and the LJ interaction, (or the electrostatic interaction) where the soft-core potentials are used, the interaction energies are calculated according to equations 9 and 26 respectively, while for other types of the interactions, the interaction energy is calculated using parameters of a conventional force field multiplied by the corresponding component coupling parameter λ.

One example of λ schedules discussed above is shown in Scheme 1 below, in which the superscript (0, 1, . . . , m, m+1, . . . , n) indicate the indexes of the reference system state, the intermediate states, and the target system state, and $\lambda_{comp}^{i}$ is the respective λ component value for state with index "i" and component "comp".

$$\lambda_{sbsA} = [\lambda_{sbsA}^0 = 1, \quad \lambda_{sbsA}^1 \quad \ldots \quad \lambda_{sbsA}^m = 0.5, \quad \lambda_{sbsA}^{m+1} \quad \ldots \quad \lambda_{sbsA}^n = 0]$$

$$\lambda_{baA} = [\lambda_{baA}^0 = 1, \quad \lambda_{baA}^1 \quad \ldots \quad \lambda_{baA}^m = 0, \quad \lambda_{baA}^{m+1} = 0 \quad \ldots \quad \lambda_{baA}^n = 0]$$

$$\lambda_{bdA} = [\lambda_{bdA}^0 = 1, \quad \lambda_{bdA}^1 \quad \ldots \quad \lambda_{bdA}^m = 0, \quad \lambda_{bdA}^{m+1} = 0 \quad \ldots \quad \lambda_{bdA}^n = 0]$$

$$\lambda_{elecA_{ex}} = [\lambda_{sbsA}^0 = 1, \quad \lambda_{elecA_{ex}}^1 = 0 \quad \ldots \quad \lambda_{elecA_{ex}}^m = 0, \quad \lambda_{elecA_{ex}}^{m+1} \quad \ldots \quad \lambda_{elecA_{ex}}^n = 1]$$

$$\lambda_{vdwA_{ex}} = [\lambda_{vdwA_{ex}}^0 = 0, \quad \lambda_{vdwA_{ex}}^1 \quad \ldots \quad \lambda_{vdwA_{ex}}^m = 1, \quad \lambda_{vdwA_{ex}}^{m+1} = 1 \quad \ldots \quad \lambda_{vdwA_{ex}}^n = 1]$$

$$\lambda_{elecA_{14}} = [\lambda_{elecA_{14}}^0 = 0, \quad \lambda_{elecA_{14}}^1 \quad \ldots \quad \lambda_{elecA_{14}}^m = 0, \quad \lambda_{elecA_{14}}^{m+1} = 0 \quad \ldots \quad \lambda_{elecA_{14}}^n = 0]$$

$$\lambda_{vdwA_{14}} = [\lambda_{vdwA_{14}}^0 = 1, \quad \lambda_{vdwA_{14}}^1 \quad \ldots \quad \lambda_{vdwA_{14}}^m = 1 \quad \lambda_{vdwA_{14}}^{m+1} \quad \ldots \quad \lambda_{vdwA_{14}}^n = 0]$$

$$\lambda_{sbsB} = [\lambda_{sbsB}^0 = 1, \quad \lambda_{sbsB}^1 \quad \ldots \quad \lambda_{sbsB}^m = 0.5, \quad \lambda_{sbsB}^{m+1} \quad \ldots \quad \lambda_{sbsB}^n = 1]$$

$$\lambda_{baB} = [\lambda_{baB}^0 = 0, \quad \lambda_{baB}^1 = 0 \quad \ldots \quad \lambda_{baB}^m = 0, \quad \lambda_{baB}^{m+1} \quad \ldots \quad \lambda_{baB}^n = 1]$$

$$\lambda_{bdB} = [\lambda_{bdB}^0 = 0, \quad \lambda_{bdB}^1 = 0 \quad \ldots \quad \lambda_{bdB}^m = 0, \quad \lambda_{bdB}^{m+1} \quad \ldots \quad \lambda_{bdB}^n = 1]$$

$$\lambda_{elecB_{ex}} = [\lambda_{elecB_{ex}}^0 = 0, \quad \lambda_{elecB_{ex}}^1 \quad \ldots \quad \lambda_{elecB_{ex}}^m = 0, \quad \lambda_{elecB_{ex}}^{m+1} \quad \ldots \quad \lambda_{elecB_{ex}}^n = 0]$$

$$\lambda_{vdwB_{ex}} = [\lambda_{vdwB_{ex}}^0 = 1, \quad \lambda_{vdwB_{ex}}^1 = 1 \quad \ldots \quad \lambda_{vdwB_{ex}}^m = 1, \quad \lambda_{vdwB_{ex}}^{m+1} \quad \ldots \quad \lambda_{vdwB_{ex}}^n = 0]$$

$$\lambda_{elecB_{14}} = [\lambda_{elecB_{14}}^0 = 1, \quad \lambda_{elecB_{14}}^1 = 0 \quad \ldots \quad \lambda_{elecB_{14}}^m = 0 \quad \lambda_{elecB_{14}}^{m+1} \quad \ldots \quad \lambda_{elecB_{14}}^n = 1]$$

$$\lambda_{vdwB_{14}} = [\lambda_{elecB_{14}}^0 = 1, \quad \lambda_{vdwB_{ex}}^1 \quad \ldots \quad \lambda_{vdwB_{ex}}^m = 1, \quad \lambda_{vdwB_{ex}}^{m+1} = 1 \quad \ldots \quad \lambda_{vdwB_{ex}}^n = 1]$$

Scheme 1

$\lambda_{sbsA}$ as shown in Scheme 1 can be varied from 1 to 0 over the bond breaking (e.g., a ring opening) transformation. In some embodiments, the variation of $\lambda_{sbsA}$ can be linear and/or monotonic over the transformation. In other embodiments, the variation of $\lambda_{sbsA}$ can be non-linear and/or non-monotonic over the transformation. Although it is shown that $\lambda_{sbsA}$=0.5 at the intermediate system state indexed by m, this schedule for $\lambda_{sbsA}$ is merely illustrative and non-limiting (e.g., other values smaller or greater than 0.5 can also be used for the intermediate system state indexed by m).

$\lambda_{baA}$ as shown in Scheme 1 can be varied from 1 to 0 over the bond breaking (e.g., a ring opening) transformation. In some embodiments, the variation of $\lambda_{baA}$ can be linear and/or monotonic over the transformation or a portion of the transformation. In other embodiments, the variation of $\lambda_{baA}$ can be non-linear and/or non-monotonic over the transformation or a portion of the transformation.

$\lambda_{bdA}$ as shown in Scheme 1 can be varied from 1 to 0 over the bond breaking (e.g., a ring opening) transformation. In some embodiments, the variation of $\lambda_{bdA}$ can be linear and/or monotonic over the transformation or a portion of the transformation. In other embodiments, the variation of $\lambda_{bdA}$ can be non-linear and/or non-monotonic over the transformation or a portion of the transformation.

Further, in certain embodiments, for improved sampling efficiency in the molecular simulations, the bonded angle and bonded dihedral interactions between two atoms can be turned off more quickly to 0 before the bonded stretch interactions are turned off during the bond breaking transformation (conversely, the bonded angle and bonded dihedral interactions can be turned on only after the bonded stretch interactions are turned on to a predetermined degree). Although it is shown that $\lambda_{baA}/\lambda_{bdA}$ can be decreased to 0 at the intermediate system state indexed by m (meaning that $\lambda_{baA}/\lambda_{bdA}$ can be varied from 1 at the initial state to 0 at this intermediate state by a more rapid decrease than that of $\lambda_{sbsA}$), the schedule for $\lambda_{baA}/\lambda_{bdA}$ are merely illustrative and non-limiting (e.g., $\lambda_{baA}/\lambda_{bdA}$ can be decreased to 0 more rapidly or slowly from the initial state). Also, the $\lambda_{baA}$ and $\lambda_{bdA}$ can be varied separately according to their own respective schedules and do not need to be synchronized.

$\lambda_{elecA_{ex}}$ as shown in Scheme 1 can be varied from 0 to 1 over the bond breaking (e.g., a ring opening) transformation. In some embodiments, the variation of $\lambda_{elecA_{ex}}$ can be linear and/or monotonic over the transformation or a portion of the transformation. In other embodiments, the variation of $\lambda_{elecA_{ex}}$ can be non-linear and/or non-monotonic over the transformation or a portion of the transformation. Although it is shown that $\lambda_{elecA_{ex}}=0$ at the intermediate system state indexed by m (i.e., $\lambda_{elecA_{ex}}$ can be 0 from the initial state through the intermediate state indexed by m, and increased from this intermediate state to the final state), this schedule is merely illustrative and non-limiting (e.g., $\lambda_{elecA_{ex}}$ can be kept at 0 until an intermediate state that precedes or subsequent to the intermediate state indexed by m).

$\lambda_{vdwA_{ex}}$ as shown in Scheme 1 can be varied from 0 to 1 over the bond breaking (e.g., a ring opening) transformation. In some embodiments, the variation of $\lambda_{vdwA_{ex}}$ can be linear and/or monotonic over the transformation or a portion of the transformation. In other embodiments, the variation of $\lambda_{vdwA_{ex}}$ can be non-linear and/or non-monotonic over the transformation or a portion of the transformation. Although it is shown that $\lambda_{vdwA_{ex}}=1$ at the intermediate system state indexed by m ($\lambda_{vdwA_{ex}}$ can be increased from the initial state at the value of 0 to the intermediate state indexed by m at the value of 1, and stay at 1 thereon until the final state), this schedule is merely illustrative and non-limiting (e.g., $\lambda_{vdwA_{ex}}$ can be increased to 1 at an intermediate state that precedes or follows the intermediate state indexed by m). Further, in certain embodiments, for improved sampling efficiency in the molecular simulations, the van der Waals interaction between two atoms can be fully turned on before the electrostatic interactions are turned on during the transformation. This is illustrated in Schedule 1, where the schedules of $\lambda_{elecA_{ex}}$ and $\lambda_{vdwA_{ex}}$ are coordinated such that when $\lambda_{vdwA_{ex}}$ is smaller than 1 for an intermediate state, $\lambda_{elecA_{ex}}$ is 0 for that intermediate state.

$\lambda_{elecA_{14}}$ as shown in Scheme 1 can be varied from 1 to 0 over the bond breaking (e.g., a ring opening) transformation. In some embodiments, the variation of $\lambda_{elecA_{14}}$ can be linear and/or monotonic over the transformation or a portion of the transformation. In other embodiments, the variation of $\lambda_{elecA_{14}}$ can be non-linear and/or non-monotonic over the transformation or a portion of the transformation. Although it is shown that $\lambda_{elecA_{14}}=0$ at the intermediate system state indexed by m (i.e., $\lambda_{elecA_{14}}$ can be varied from 1 at the initial state to 0 at this intermediate state by a more rapid decrease than that of $\lambda_{sbsA}$), this schedule is merely illustrative and non-limiting (e.g., $\lambda_{elecA_{14}}$ can be decreased to 0 more rapidly or slowly from the initial state).

$\lambda_{vdwA_{14}}$ as shown in Scheme 1 can be varied from 1 to 0 over the bond breaking (e.g., a ring opening) transformation. In some embodiments, the variation of $\lambda_{vdwA_{14}}$ can be linear and/or monotonic over the transformation or a portion of the transformation. In other embodiments, the variation of $\lambda_{vdwA_{14}}$ can be non-linear and/or non-monotonic over the transformation or a portion of the transformation. Although it is shown that $\lambda_{vdwA_{14}}=1$ at the intermediate system state indexed by m ($\lambda_{vdwA_{14}}$ can be kept at 1 from the initial state through the intermediate state indexed by m, and then decreased to 0 from that intermediate state to the final state), this schedule is merely illustrative and non-limiting (e.g., $\lambda_{vdwA_{14}}$ can be kept to 1 from the initial state through an intermediate state that precedes or follows the intermediate state indexed by m, and then decreased to 0 from that intermediate state to the final state). Further, in certain embodiments, for improved sampling efficiency in the molecular simulations, the van der Waals interactions between two atoms are turned off only after the electrostatic interactions are fully turned off during the transformation. This is illustrated in Schedule 1, where the schedules of $\lambda_{elecA_{14}}$ and $\lambda_{vdwA_{14}}$ are coordinated such that when $\lambda_{vdwA_{14}}$ is smaller than 1 for an intermediate state, $\lambda_{elecA_{14}}$ is 0 for that intermediate state.

The schedules of the λ components for the bond formation transformation, $\lambda_{sbsB}$, $\lambda_{baB}$ and $\lambda_{bdB}$, $\lambda_{elecB_{ex}}$ and $\lambda_{vdwB_{ex}}$, $\lambda_{elecB_{14}}$ and $\lambda_{vdwB_{14}}$ can be readily understood by a person of ordinary skill in the art in view of the above description of the λ schedule for the bond breaking transformation, as the two transformation processes are essentially reverse to each other. It is noted, however, that although the values of a λ component in the bond formation and the corresponding λ component in the bond breaking transformation (e.g., $\lambda_{sbsA}$ and $\lambda_{sbsB}$) appear to sum up to 1, this is merely illustrative. For any given system, a bond cannot be both forming and breaking simultaneously in the same alchemical transformation considered in this application. Thus, the λ component schedules in a bond breaking transformation do not need to coordinate with those in bond formation transformation. As an example, $\lambda_{sbsB}$ can follow a schedule of increasing from 0 to 1 in a non-linear manner while $\lambda_{sbsA}$ follows a schedule of decreasing from 1 to 0 in a linear manner. Further, as shown in FIG. 1c., this application contemplates the breaking of one bond (e.g., the bond between $A_1$ and $A_4$) and the simultaneous formation of another bond (or bonds) (e.g., the bond between $A_1$ and $A_{13}$ and the bond between $A_4$ and $A_{13}$). In this case, the λ component schedules for the bond breaking transformation and the λ component schedules for the bond formation transformation can be selected separately and not dependent upon each other.

In the following, energy calculations in a molecular simulation of the transformation shown in FIG. 1a are illustrated in connection with certain embodiments of the above-described λ schedule.

Bonded stretch interactions that are affected by the bond formation between $A_1$ and $A_3$ in FIG. 1a: $(A_1,A_3)$ Bonded angle interactions that are affected by the bond formation between $A_1$ and $A_3$ in FIG. 1a:
  (i) Bonded angle interactions only appearing in the initial state and not in the final state: $(A_2,A_1,A_{10})$, $(A_4,A_1,A_{10})$, $(A_5,A_1,A_{10})$, $(A_2,A_3,A_{11})$, $(A_8,A_3,A_{11})$, $(A_9,A_3,A_{11})$;
  (ii) Bonded angle interactions only appearing in the final state and not in the initial state: $(A_2,A_3,A_3)$, $(A_4,A_1,A_3)$, $(A_5,A_1,A_3)$, $(A_1,A_3,A_2)$, $(A_1,A_3,A_8)$, $(A_1,A_3,A_9)$.

Bonded dihedral interactions that are affected by the bond formation between $A_1$ and $A_3$ in FIG. 1a:

(i) Bonded dihedral angle interactions involving atoms only appearing in the initial state and not in the final state: $(A_{10},A_1,A_2,A_3)$, $(A_{10},A_1,A_2,A_6)$, $(A_{10},A_1,A_2,A_7)$, $(A_1,A_2,A_3,A_{11})$, $(A_6,A_2,A_3,A_{11})$, $(A_7,A_2,A_3,A_{11})$;

(ii) Bonded dihedral angle interactions involving atoms only appearing in the final state and not in the initial state: $(A_3,A_1,A_2,A_6)$, $(A_3,A_1,A_2,A_7)$, $(A_2,A_1,A_3,A_8)$, $(A_2,A_1,A_3,A_9)$, $(A_4,A_1,A_3,A_2)$, $(A_4,A_1,A_3,A_8)$, $(A_4,A_1,A_3,A_9)$, $(A_5,A_1,A_3,A_2)$, $(A_5,A_1,A_3,A_8)$, $(A_5,A_1,A_3,A_9)$, $(A_6,A_2,A_3,A_1)$, $(A_7,A_2,A_3,A_1)$.

Atom pairs excluded for the calculation of nonbonded interactions in the initial state but not excluded in the final state in FIG. 1a: $(A_1,A_{10})$, $(A_1,A_{11})$, $(A_2,A_{10})$, $(A_2,A_{11})$, $(A_3,A_{10})$, $(A_3,A_{11})$, $(A_4,A_{10})$, $(A_5,A_{10})$, $(A_6,A_{10})$, $(A_6,A_{11})$, $(A_7,A_{10})$, $(A_7,A_{11})$, $(A_8,A_{11})$, $(A_9,A_{11})$.

Atom pairs excluded for the calculation of nonbonded interactions in the final state but not excluded in the initial state in FIG. 1a: $(A_4,A_8)$, $(A_4,A_9)$, $(A_5,A_8)$, $(A_5,A_9)$.

1-4 atom pairs included in the initial state but not included in the final state in FIG. 1a: $(A_1,A_8)$, $(A_1,A_9)$, $(A_3,A_4)$, $(A_3,A_5)$.

1-4 atom pairs included in the final state but not included in the initial state in FIG. 1a: $(A_4,A_8)$, $(A_4,A_9)$, $(A_5,A_8)$, $(A_5,A_9)$.

The other bonded and nonbonded interactions that are not affected by the formation and annihilation of bonds for the ring opening or closing transformation can be modulated by a regular $\lambda$ schedule as in conventional free energy perturbations not involving ring opening and closing (e.g., incrementing $\lambda_{other}$ from the initial state to the final state, where the interactions between $P_{AB}$ and $P_A$ is scaled by $1-\lambda_{other}$, and the interactions between $P_{A\bar{B}}$ and $P_B$ is scaled by $\lambda_{other}$). Further, all the interactions involving atoms that only appear in the initial state but missing from the final state (i.e., those atoms that become "dummy" atoms in the final state) will also be treated by a normal $\lambda$ schedule. Conversely, for the reverse (bond formation) transformation, all the interactions involving atoms that appear only in the final state and are missing from the initial state (e.g., $A_{11}$ and $A_{12}$ in FIG. 1a) will also be treated by the normal $\lambda$ schedule. The remaining interactions, i.e., those affected by the formation and annihilation of bonds for the ring opening or closing transformation that do not involve atoms that only appear in the initial state or only appear in the final state can be modulated by a "special" $\lambda$ schedule similar to what is described in Schedule 1, that is, for the ring closing transformation depicted in FIG. 1a:

Bonded stretch interaction included in the initial state but not in the final state is modulated by $\lambda_{sbsA}$ using a soft bond interaction potential described herein (in this example, no interaction belongs to this category);

Bonded stretch interaction not included in the initial state but included in the final state is modulated by $\lambda_{sbsB}$ using a soft bond interaction potential described herein (in this example, the bonded stretch interaction between atoms $A_1$ and $A_3$ belong to this category);

Bonded angle interactions included in the initial state but not in the final state are modulated by $\lambda_{baA}$ (in this example, no interaction belongs to this category);

Bonded angle interactions included in the final state but not in the initial state are modulated by $\lambda_{baB}$ (in this example, the bonded angle interactions between atoms $(A_2,A_1,A_3)$, $(A_4,A_1,A_3)$, $(A_5,A_1,A_3)$, $(A_1,A_3,A_2)$, $(A_1,A_3,A_8)$, $(A_1,A_3,A_9)$ belong to this category);

Bonded dihedral angle interactions included in the initial state but not in the final state are modulated by $\lambda_{bdA}$ (in this example, no interaction belongs to this category);

Bonded dihedral angle interactions included in the final state but not in the initial state are modulated by $\lambda_{bdB}$ (in this example, the bonded dihedral angle interactions between atoms $(A_3,A_1,A_2,A_6)$, $(A_3,A_1,A_2,A_7)$, $(A_2,A_1,A_3,A_8)$, $(A_2,A_1,A_3,A_9)$, $(A_4,A_1,A_3,A_2)$, $(A_4,A_1,A_3,A_8)$, $(A_4,A_1,A_3,A_9)$, $(A_5,A_1,A_3,A_2)$, $(A_5,A_1,A_3,A_8)$, $(A_5,A_1,A_3,A_9)$, $(A_6,A_2,A_3,A_1)$, $(A_7,A_2,A_3,A_1)$ belong to this category);

Interactions excluded in the initial state but not excluded in the final state are modulated by $\lambda_{elecAex}$ and $\lambda_{vdwAex}$ (in this example, no interaction belongs to this category);

Interactions excluded in the final state but not excluded in the initial state are modulated by $\lambda_{elecBex}$ and $\lambda_{vdwBex}$ (in this example, the interactions excluded in the final state for pairs $(A_4,A_8)$, $(A_4,A_9)$, $(A_5,A_8)$, $(A_5,A_9)$ belong to this category);

1-4 pair interactions included in the initial state but not in the final state are modulated by $\lambda_{elecA14}$ and $\lambda_{vdwA14}$ (in this example, the 1-4 pair interactions for pairs $(A_1,A_8)$, $(A_1,A_9)$, $(A_3,A_4)$, $(A_3,A_5)$ belong to this category); and 1-4 pair interactions included in the final state but not in the initial state are modulated by $\lambda_{elecB14}$ and $\lambda_{vdwB14}$ (in this example, the 1-4 pair interactions for pairs $(A_4,A_8)$, $(A_4,A_9)$, $(A_5,A_8)$, $(A_5,A_9)$ belong to this category).

With the energy terms defined by a suitable $\lambda$ schedule (such as the one depicted in Scheme 1) for all the system states in the transformation from the initial state to the final state, molecular simulations can be run to sample the ensembles of micro-states obtained at the reference state, the target state, and the intermediate states according to the $\lambda$ schedule. For each $\lambda$ window, the free energy difference can be calculated between all the neighboring lambda windows $\Delta F_{\lambda i \to \lambda i+1}$ and/or between any pair of lambda windows $\Delta F_{i \to j}$, including between the reference state and the target state. The total free energy difference between the reference state and the target state can be obtained by adding the free energy differences between each two successive state along the transformation path defined by the $\lambda$ schedule or directly obtained by analyzing the data from all the sampled states.

The free energy difference between neighboring $\lambda$ windows or generally between any pair of states including initial state and the final state can be calculated by a variety of ways. For example, e.g., by the use of internal energy difference (FEP NVT ensemble), the enthalpy difference (FEP NPT ensemble), or other related thermodynamic property difference (FEP other ensembles, such as the NVE ensemble), of a suitable ensemble of the micro-states obtained at the target state, the reference state, and the intermediate states as coupling parameter $\lambda$ is instantaneously varied for the selected ensemble of micro-states. The analysis can be further performed, for example, by way of Bannet Acceptance Ratio (BAR), Multistate Bannet Acceptance Ratio (MBAR), Weighted Histogram Analysis Method (WHAM), Zwanzig averaging, or other similar FEP-family estimators. Alternatively, the free energy difference between neighboring $\lambda$ windows or generally between any pairs of states including the initial state and the final state can be calculated by way of an analysis the derivative of the energy with respect of the coupling vector $\lambda$ (TI NVT ensemble), the derivative of the enthalpy with respect to the coupling vector λ (TI NPT ensemble), or the derivative of other related thermodynamic properties with respect to the coupling vector λ (TI other ensembles, such as the TI NVE ensemble), for each microscopic state obtained. In other embodiments, the free energy difference of each λ window can be calculated by way of an analysis of the potential of mean force (PMF) associated with sampling of the coupling vector λ as a dynamical variable that can dynamically transition between the reference state, the target state and intermediate states for example and without loss of generality via the λ-dynamics, the principle of which is generally described in Knight et al., λ-dynamics free energy simulation methods, J. Comput. Chem., 2009, 30: 1692-1700, the disclosure of which is incorporated by reference herein. λ-dynamics based sampling methods include, but are not limited to, λ-Monte Carlo, λ-metadynamics, λ-OSRW, and other λ PMF sampling family methods.

Figure 4:
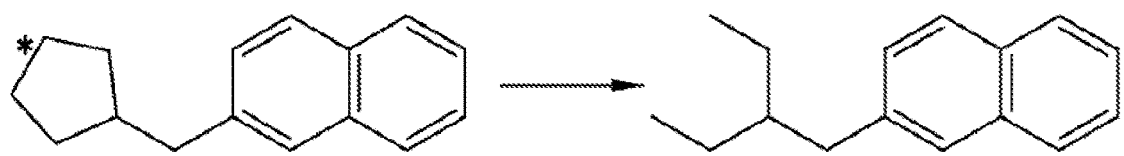
FIG. 4 is a diagram showing an illustrative ring-opening transformation occurring in a cyclic structure, the free energy change of which is amenable to the application of embodiments of the present invention.
Figure 5:
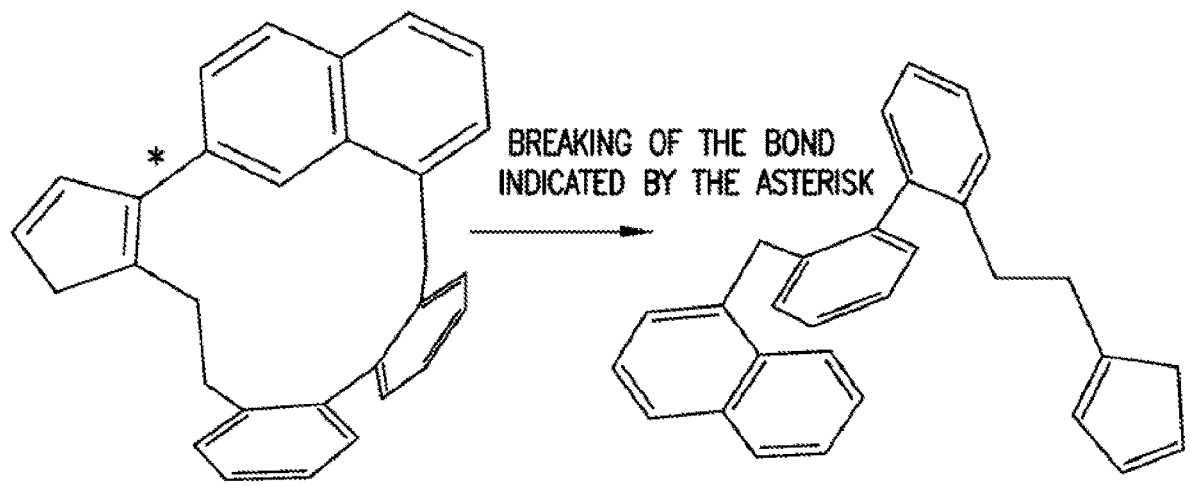
FIG. 5 is a diagram showing an illustrative bond breaking between two connected ring structures, the free energy change of which is amenable to the application of embodiments of the present invention.
Figure 6:
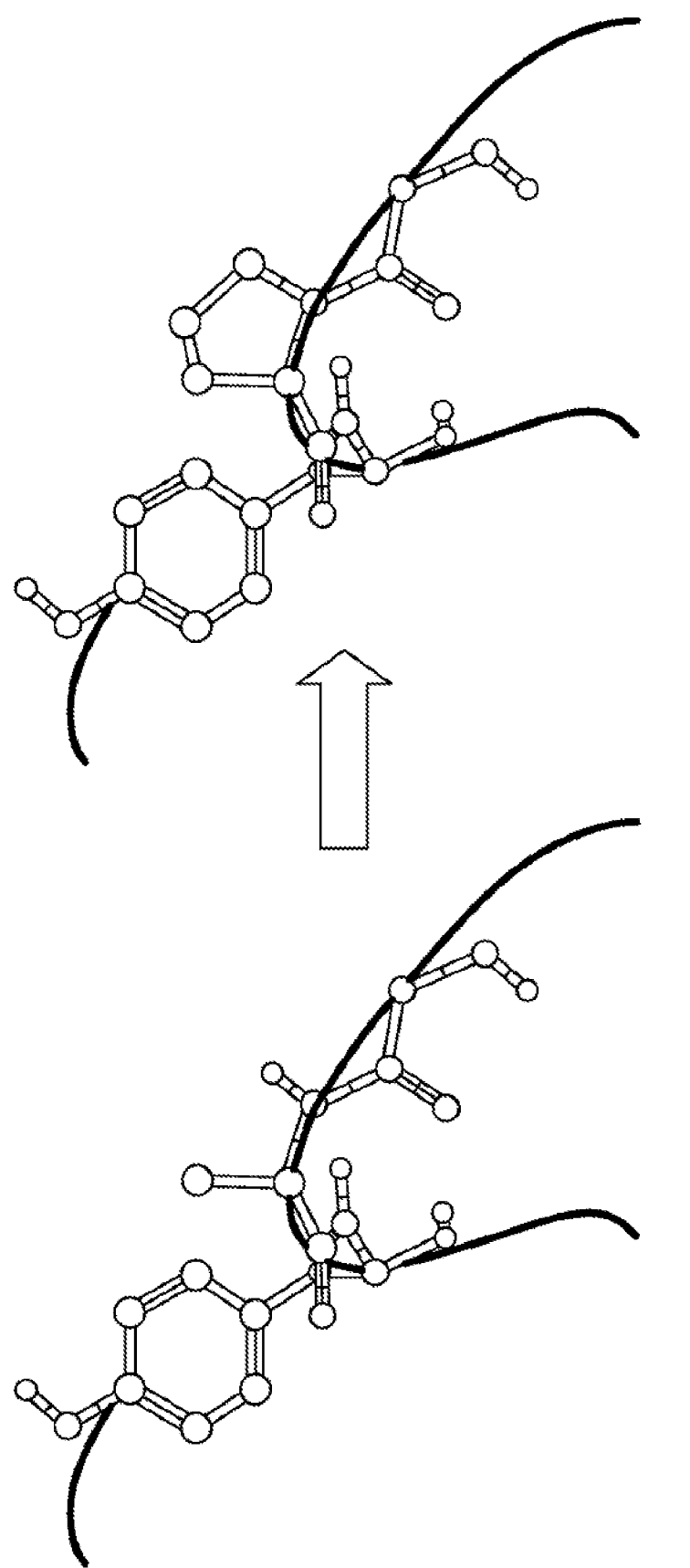
FIG. 6 is a depiction of a protein residue mutation transformation where a non-proline residue in the reference system is transformed into a proline residue in the target system, the free energy change of which is amenable to the application of embodiments of the present invention.
Figure 7:
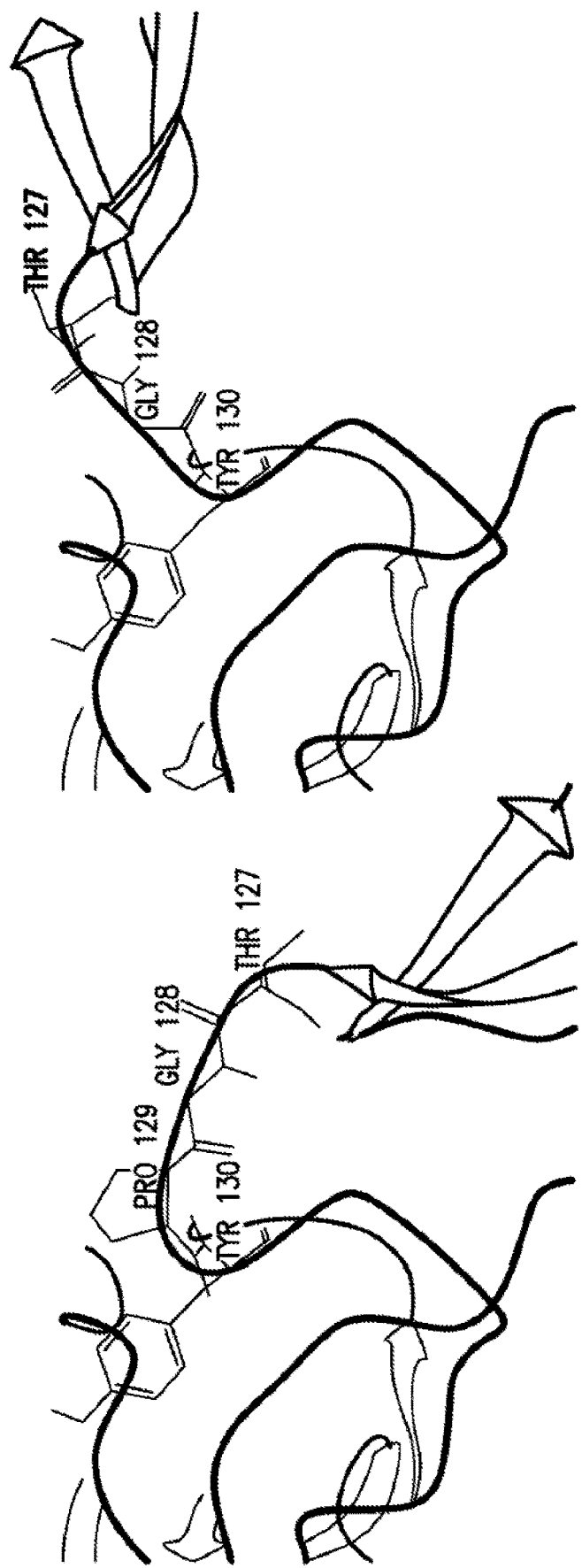
FIG. 7 is a depiction of a protein residue deletion transformation where a residue (proline) in the reference system is deleted in the target system, resulting in a direct connection between its two neighboring residues, the free energy change of which is amenable to the application of embodiments of the present invention.

The methods for free energy difference calculations described herein can be applied to a number of highly useful applications, which include, for example:

Relative protein-ligand binding affinity and/or relative solvation free energy calculations between congeneric ligands with ring opening or closing (see FIG. 4);

Relative protein-ligand binding affinity and/or relative solvation free energy calculations between congeneric ligands that differ by a macrocyclization (see FIG. 5);

The calculation of the effect of a non-proline to proline or proline to non-proline residue mutation to protein thermodynamic stability, protein-ligand binding affinity, or protein-protein binding affinity (see FIG. 6); and The calculation of the effect of a residue insertion or residue deletion to protein thermodynamic stability, protein-ligand binding affinity, or protein-protein binding affinity (see FIG. 7, which schematically shows a transformation of the illustrative protein segment structure depicted on the left by losing a residue numbered 129, resulting in the structure depicted on the right).

Embodiments of the method for the free energy calculations of the disclosed subject matter can be implemented in a computer program, which can take the form of a software component of a suitable hardware platform, for example, a standalone computer, a networked computer, a network server computer, a handheld device, or the like. Different aspects of the disclosed methods may be implemented in different software modules and executed by one processor or different processors, sequentially or in parallel, depending on how the software is designed. The apparatus on which the program can be executed can include one or more processors, one or more memory devices (such as ROM, RAM, flash memory, hard drive, optical drive, etc.), input/output devices, network interfaces, and other peripheral devices. A computer readable non-transitory media storing the program is also provided.

The disclosed subject matter is not to be limited in scope by the specific embodiments described herein. Indeed, various modifications of the disclosed subject matter in addition to those described herein will become apparent to those skilled in the art from the foregoing description and the accompanying figures. Such modifications therefore fall within the scope of the appended claims.

What is claimed is:

1. A method of rational drug design comprising:
identifying a biomolecular target molecule associated with a pathology;
identifying a small molecule candidate for binding to the biomolecular target;
calculating, using a computer, a relative binding affinity between the small molecule candidate and the biomolecular target molecule based on a free energy difference between a reference state and a target state, wherein the reference state and target state each correspond to a respective arrangement of the biomolecular target molecule and small molecule candidate that include a common set of atoms $P_{AB}$, and wherein the reference state further includes a set of atoms $P_A$, the target state further includes a set of atoms $P_B$, the set $P_A$ being present only in the reference state and not in the target state, and the set $P_B$ being present only in the target state and not the reference state, where there exist at least two atoms $A_a$ and $A_b$, $A_a$ and $A_b$ being either: (1) not valence-bonded to each other in the reference state and valence-bonded in the target state, or (2) valence-bonded to each other in reference state and not valence-bonded to each other in the target state, the method comprising:

(a) providing a topology, including the bonded connections between the atoms and the relative spatial arrangements of the atoms, for all the atoms in $P_A$, $P_B$, and $P_{AB}$;

(b) determining one or more intermediate system states along a transformation path between the reference state and the target state, the transformation path defined by a coupling parameter λ that modulates the energies arising from inter-atom interactions for each system state, the coupling parameter λ including a plurality of components each having a value belonging to [0,1] and modulating a different type of interaction energy;

(c) performing, using at least one computer processor, molecular simulations to obtain ensembles of microstates for the reference state, the target state, and the intermediate states, wherein performing molecular simulations for each of the system states includes calculating a bonded stretch interaction energy between the atoms $A_a$ and $A_b$, the bonded stretch interaction energy being defined by a soft bond potential, wherein the soft bond potential is a function of a bonded stretch component, $\lambda_{sbs}$, of the coupling parameter λ, and does not include any singular regions for all values of $\lambda_{sbs}$ within [0,1] and for all values of the distance r between $A_a$ and $A_b$, the soft bond potential further satisfies the following conditions: when $\lambda_{sbs}$ is within (0,1), the soft bond potential is flat when the distance between $A_a$ and $A_b$ approaches infinity; when $A_a$ and $A_b$ are not valence bonded in either the reference state or the target state, the soft bond potential is flat and zero for all distances between $A_a$ and $A_b$; and when $A_a$ and $A_b$ are valence bonded in either the target state or the reference state, the soft bond potential reverts to a harmonic potential; and wherein the soft bond potential is a function of $(r-r_0)^2$, where $r_0$ is the equilibrium distance between $A_a$ and $A_b$, and is expressed by:

$$U_{sbs}(r, \lambda_{sbs}) = \frac{1}{2} kf(\lambda_{sbs})(r-r_0)^2 \frac{1}{1 + g(\lambda_{sbs})\alpha(k, \lambda_{sbs})(r-r_0)^2}$$

where k is a constant, and the functions f, g and α are each continuous functions and satisfy the following conditions:

$f(\lambda_{sbs}=0)=0$, $f(\lambda_{sbs}=1)=1$, $g(\lambda_{sbs}=0)=1,$ $g(\lambda_{sbs}=1)=0,$ $\alpha(k, \lambda_{sbs}<1)>0;$ (d) calculating, using at least one computer processor, the free energy difference between the reference state and the target state, by way of an analysis of the ensembles of micro-states obtained at the target state, the reference state, and the intermediate states; and (e) determining a relative binding affinity for the biomolecular target molecule and small molecule candidate based on the calculated free energy difference;

synthesizing the small molecule candidate based on the calculation; and further assessing the small molecule candidate for suitability for treating the pathology based on assays using the synthesized small molecule candidate.

2. The method of claim 1, wherein $f(\lambda_{sbs})=\lambda_{sbs}$, $g(\lambda_{sbs})=1-\lambda_{sbs}$, and $\alpha(k, \lambda_{sbs})=$const.

3. The method of claim 1, wherein performing molecular simulations for each of the system states comprises:

if $A_a$ and $A_b$ are valence-bonded to each other in the reference state and not valence-bonded in the target state, using a schedule of $\lambda_{sbsA}$ and a corresponding soft bond potential for calculating the bonded stretch interaction energy between $A_a$ and $A_b$ for each of the intermediate states, wherein $\lambda_{sbsA}$ is 1 at the reference state, 0 at the target state, and varied from 1 to 0 at each intermediate state along the transformation from the reference state to the target state;

if $A_a$ and $A_b$ are not valence-bonded to each other in the reference state and valence-bonded in the target state, using a schedule of $\lambda_{sbsB}$ and a corresponding soft bond potential for each of the intermediate states and a soft bond potential corresponding to the $\lambda_{sbsB}$ for calculating the bonded stretch interaction between $A_a$ and $A_b$, wherein $\lambda_{sbsB}$ is 0 at the reference state, 1 at the target state, and varied from 0 to 1 at each intermediate state along the transformation from the reference state to the target state.

4. The method of claim 3, wherein performing molecular simulations for each of the system states further comprises:

(a) computing a bonded angle interaction, using applicable parameters for bonded angle interactions of a force field, between (i) a bond formed by $A_a$ and another atom $A_c$, and (ii) the bond between $A_a$ and $A_b$ that is being broken or formed by the transformation from the reference state to the target state;

(b) if $A_a$ and $A_b$ are valence-bonded to each other in the reference state and not valence-bonded to each other in the target state, multiplying the computed bonded angle interaction obtained in (a) by a bonded angle coupling parameter $\lambda_{baA}$, wherein $\lambda_{baA}$ is 1 at the reference state, 0 at the target state, and varied from 1 to 0 at each intermediate state along the transformation from the reference state to the target state; and if $A_a$ and $A_b$ are not valence-bonded to each other in the reference state and valence-bonded to each other in the target state, multiplying the computed bonded angle interaction obtained in (a) by a bonded angle coupling parameter $\lambda_{baB}$, wherein $\lambda_{baB}$ is 0 at the reference state, 1 at the target state, and varied from 0 to 1 at each intermediate state along the transformation from the reference state to the target state; and (c) including the bonded angle interaction obtained in (b) into the total energy of a simulation step of the corresponding system state.

5. The method of claim 4, wherein performing molecular simulations for each of the system states further includes:

(a) computing a dihedral angle interaction, using applicable parameters for dihedral interactions of a force field, of a group of four connected atoms $\{A_i, A_j, A_k, A_l\}$, the group including both $A_a$ and $A_b$;

(b) if $A_a$ and $A_b$ are valence-bonded to each other in the reference state and not valence-bonded to each other in the target state, multiplying the computed dihedral interaction obtained in (a) by a dihedral angle coupling parameter $\lambda_{bdA}$, wherein $\lambda_{bdA}$ is 1 at the reference state, 0 at the target state, and varied from 1 to 0 at each intermediate state along the transformation from the reference state to the target state; and if $A_a$ and $A_b$ are not valence-bonded to each other in the reference state and valence-bonded to each other in the target state, multiplying the computed dihedral interaction obtained in (a) by a dihedral angle coupling parameter $\lambda_{bdB}$, wherein $\lambda_{bdB}$ is 0 at the reference state, 1 at the target state, and varied from 0 to 1 at each intermediate state along the transformation from the reference state to the target state; and (c) including the dihedral interaction obtained in (b) into the total energy of the simulation step of the corresponding system state.

6. The method of claim 5, wherein:

if $A_a$ and $A_b$ are valence-bonded to each other in the reference state and not valence-bonded to each other in the target state, the bonded angle interaction and the bonded dihedral interaction coupling parameters $\lambda_{baA}$ and $\lambda_{bdA}$, are each selected to be 0 when $\lambda_{sbsA}$ is smaller than a predefined threshold, and if $A_a$ and $A_b$ are not valence-bonded to each other in the reference state and valence-bonded to each other in the target state, the bonded angle interaction and the bonded dihedral interaction coupling parameters $\lambda_{baB}$ and $\lambda_{bdB}$ are each selected to be 0 when $\lambda_{sbsB}$ is smaller than a predefined threshold.

7. The method of claim 5, wherein performing molecular simulations for all of the states further includes:

(a) computing nonbonded electrostatic interactions and van der Waals interactions, using applicable parameters for electrostatic interactions and van der Waals of a force field, between two atoms $A_i$ and $A_j$ and the non-bonded exclusion status of the pair $(A_i, A_j)$ is affected by the transformation from the reference state to the target state;

(b) if $A_a$ and $A_b$ are valence-bonded to each other in the reference state and not valence-bonded in the target state, and the nonbonded interactions between $A_i$ and $A_j$ are excluded in the reference state but not excluded in the target state, multiplying the nonbonded electrostatic interactions and van der Waals interactions between $A_i$ and $A_j$ obtained in (a) by coupling parameters $\lambda_{elecAex}$ and $\lambda_{vdwAex}$, respectively, wherein both of $\lambda_{elecAex}$ and $\lambda_{vdwAex}$ are 0 at the reference state, 1 at the target state, and varied from 0 to 1 at each intermediate state along the transformation from the reference state to the target state;

if $A_a$ and $A_b$ are not valence-bonded to each other in the reference state and valence-bonded in the target state, and the nonbonded interactions between $A_i$ and $A_j$ are not excluded in the reference state but excluded in the target state, multiplying the nonbonded electrostatic interactions and van der Waals interactions between $A_i$ and $A_j$ obtained in (a) by coupling parameters $\lambda_{elecBex}$ and $\lambda_{vdwBex}$, respectively, wherein both of $\lambda_{elecBex}$ and $\lambda_{vdwBex}$ are 1 at the reference state, 0 at the target state, and varied from 1 to 0 at each intermediate state along the transformation from the reference state to the target state; and (c) including the calculated nonbonded electrostatic interactions and van der Waals interactions obtained in (b) into the total energy of the simulation step of the corresponding system state.

8. The method of claim 7, wherein performing molecular simulations for all of the states further includes:

if $A_a$ and $A_b$ are valence-bonded to each other in the reference state and not valence-bonded in the target state, and the nonbonded interactions between $A_i$ and $A_j$ are excluded in the reference state but not excluded in the target state, varying each of $\lambda_{elecAex}$ and $\lambda_{vdwAex}$ according to a schedule for each of the intermediate states along the transformation from the reference state to the target state such that when $\lambda_{vdwAex}$ is smaller than 1 for an intermediate state, $\lambda_{elecAex}$ is 0 for that intermediate state; and if $A_a$ and $A_b$ are not valence-bonded to each other in the reference state and valence-bonded in the target state, and the nonbonded interactions between $A_i$ and $A_j$ are not excluded in the reference state but excluded in the target state, varying each of $\lambda_{elecBex}$ and $\lambda_{vdwBex}$ according to a schedule for each of the intermediate states along the transformation from the reference state to the target state such that when $\lambda_{vdwAex}$ is smaller than 1 for an intermediate state, $\lambda_{elecAex}$ is 0 for that intermediate state.

9. The method of claim 7, wherein performing molecular simulations for all of the states further includes:

(a) computing nonbonded electrostatic 1-4 pair interactions and van der Waals 1-4 pair interactions, using applicable parameters for electrostatic 1-4 pair interactions and van der Waals 1-4 pair interactions of a force field, between two atoms $A_i$ and $A_j$ which together with another two intervening atoms forms a bonded dihedral angle interaction in either the reference state or the target state;

(b) if $A_a$ and $A_b$ are valence-bonded to each other in the reference state and not valence-bonded in the target state:

if the nonbonded 1-4 pair interactions between $A_i$ and $A_j$ are included in the reference state but not included in the target state, multiplying the nonbonded electrostatic 1-4 pair interactions and van der Waals 1-4 pair interactions between $A_i$ and $A_j$ obtained in (a) by coupling parameters $\lambda_{elecA14}$ and $\lambda_{vdwA14}$, respectively, wherein both of $\lambda_{elecA14}$ and $\lambda_{vdwA14}$ are 1 at the reference state, 0 at the target state, and varied from 1 to 0 at each intermediate state along the transformation from the reference state to the target state, and if the nonbonded 1-4 pair interactions between $A_i$ and $A_j$ are not included in the reference state but included in the target state, multiplying the nonbonded electrostatic 1-4 pair interactions and van der Waals 1-4 pair interactions between $A_i$ and $A_j$ obtained in (a) by coupling parameters $\lambda_{elecB14}$ and $\lambda_{vdwB14}$, respectively, wherein both of $\lambda_{elecB14}$ and $\lambda_{vdwB14}$ are 0 at the reference state, 1 at the target state, and varied from 0 to 1 at each intermediate state along the transformation from the reference state to the target state, and if $A_a$ and $A_b$ are not valence-bonded to each other in the reference state and valence-bonded in the target state:

if the nonbonded 1-4 pair interactions between $A_i$ and $A_j$ are not included in the reference state but included in the target state, multiplying the nonbonded electrostatic 1-4 pair interactions and van der Waals 1-4 pair interactions between $A_i$ and $A_j$ obtained in (a) by coupling parameters $\lambda_{elecB14}$ and $\lambda_{vdwB14}$, respectively, wherein both of $\lambda_{elecB14}$ and $\lambda_{vdwB14}$ are 0 at the reference state, 1 at the target state, and varied from 0 to 1 at each intermediate state along the transformation from the reference state to the target state, and if the nonbonded 1-4 pair interactions between $A_i$ and $A_j$ are included in the reference state but not included in the target state, multiplying the nonbonded electrostatic 1-4 pair interactions and van der Waals 1-4 pair interactions between $A_i$ and $A_j$ obtained in (a) by the coupling parameters $\lambda_{elecA14}$ and $\lambda_{vdwA14}$, respectively, wherein both of $\lambda_{elecA14}$ and $\lambda_{vdwA14}$ are 1 at the reference state, 0 at the target state, and varied from 1 to 0 at each intermediate state along the transformation from the reference state to the target state; and (c) including the calculated electrostatic 1-4 pair interactions and van der Waals 1-4 pair interactions obtained in (b) into the total energy of the simulation step of the corresponding system state.

10. The method of claim 9, wherein performing molecular simulations for all of the states further includes:

if $A_a$ and $A_b$ are valence-bonded to each other in the reference state and not valence-bonded in the target state, if the nonbonded 1-4 pair interactions between $A_i$ and $A_j$ are included in the reference state but not included in the target state, varying each of $\lambda_{elecA14}$ and $\lambda_{vdwA14}$ according to a schedule for each of the intermediate states along the transformation from the reference state to the target state such that when $\lambda_{vdwA14}$ is smaller than 1 for an intermediate state, $\lambda_{elecA14}$ is 0 for that intermediate state;

if the nonbonded 1-4 pair interactions between $A_i$ and $A_j$ are not included in the reference state but included in the target state, varying each of $\lambda_{elecB14}$ and $\lambda_{vdwB14}$ according to a schedule for each of the intermediate states along the transformation from the reference state to the target state such that when $\lambda_{vdwB14}$ is smaller than 1 for an intermediate state, $\lambda_{elecB14}$ is 0 for that intermediate state; and if $A_a$ and $A_b$ are not valence-bonded to each other in the reference state and valence-bonded in the target state, if the nonbonded 1-4 pair interactions between $A_i$ and $A_j$ are not included in the reference state but included in the target state, varying each of $\lambda_{elecB14}$ and $\lambda_{vdwB14}$ according to a schedule for each of the intermediate states along the transformation from the reference state to the target state such that when $\lambda_{vdwB14}$ is smaller than 1 for an intermediate state, $\lambda_{elecB14}$ is 0 for that intermediate state;

if the nonbonded 1-4 pair interactions between $A_i$ and $A_j$ are included in the reference state but not included in the target state, varying each of $\lambda_{elecA14}$ and $\lambda_{vdwA14}$ according to a schedule for each of the intermediate states along the transformation from the reference state to the target state such that when $\lambda_{vdwA14}$ is smaller than 1 for an intermediate state, $\lambda_{elecA14}$ is 0 for that intermediate state.

11. The method of claim 7, wherein at least one of the computing of the van der Waals interactions includes using a soft-core LJ interaction potential.

12. The method of claim 1, wherein at least one of the reference state and the target state includes a molecule having a ring structure in which the atoms $A_a$ and $A_b$ are bonded to each other and form a part of the ring structure.

13. The method of claim 1, wherein the molecular simulations include at least one of molecular dynamic simulations and Monte Carlo simulations.

14. The method of claim 1, wherein calculating the free energy difference between the reference state and the target state comprises performing an analysis of the ensembles of micro-states obtained at the target state, the reference state, and the intermediate states by way of a determination and analysis of the work associated with the variation of coupling parameter $\lambda$.

15. The method of claim 1, wherein calculating the free energy difference between the reference state and the target state comprises performing an analysis of the ensembles of micro-states obtained at the target state, the reference state, and the intermediate states by way of an analysis of the differences in a thermodynamic property of an ensemble of the micro-states obtained at the target state, the reference state, and the intermediate states as coupling parameter $\lambda$ is instantaneously varied for the selected ensemble of micro-states.

16. The method of claim 15, wherein the ensemble is selected from an NVT ensemble, a NPT ensemble, a NVE ensemble, and a μVT ensemble.

17. The method of claim 15, wherein performing the analysis of the differences in a thermodynamic property comprises applying an estimator selected from BAR, MBAR, WHAM, Zwanzig average estimators.

18. The method of claim 15, wherein performing the analysis of the differences in a thermodynamic property comprises applying one of an FEP-family estimators.

19. The method of claim 1, wherein calculating the free energy difference between the reference state and the target state comprises performing a thermodynamic integration analysis of the derivative of a thermodynamic property of an ensemble of micro-states obtained for the target state, the reference state, and the intermediate states with respect of the coupling parameter $\lambda$.

20. The method of claim 19, wherein the ensemble is selected from an NVT ensemble, a NPT ensemble, a NVE ensemble, and a μVT ensemble.

21. The method of claim 1, wherein at least one of $P_A$ and $P_B$ is null.

* * * * *